US009345715B2

(12) United States Patent
Young et al.

(10) Patent No.: US 9,345,715 B2
(45) Date of Patent: *May 24, 2016

(54) METHODS OF TREATING DIABETES OR OBESITY USING BILE ACIDS, BILE SALTS, AND MIMICS THEREOF

(71) Applicant: Satiogen Pharmaceuticals, Inc., San Diego, CA (US)

(72) Inventors: Andrew A. Young, Chapel Hill, NC (US); Bronislava Gedulin, Del Mar, CA (US); Howard E. Greene, Frankfort, MI (US)

(73) Assignee: SATIOGEN PHARMACEUTICALS, INC., San Diego, CA (US)

( * ) Notice: Subject to any disclaimer, the term of this patent is extended or adjusted under 35 U.S.C. 154(b) by 509 days.

This patent is subject to a terminal disclaimer.

(21) Appl. No.: 13/673,820

(22) Filed: Nov. 9, 2012

(65) Prior Publication Data

US 2013/0190281 A1    Jul. 25, 2013

Related U.S. Application Data

(63) Continuation of application No. 12/624,345, filed on Nov. 23, 2009, now Pat. No. 8,318,663.

(60) Provisional application No. 61/118,324, filed on Nov. 26, 2008, provisional application No. 61/255,211, filed on Oct. 27, 2009.

(51) Int. Cl.
| | |
|---|---|
| *A61K 38/00* | (2006.01) |
| *A61K 31/58* | (2006.01) |
| *A61K 31/575* | (2006.01) |
| *A61K 9/00* | (2006.01) |
| *A61K 9/20* | (2006.01) |
| *A61K 9/28* | (2006.01) |
| *A61K 35/413* | (2015.01) |
| *A61K 45/06* | (2006.01) |

(52) U.S. Cl.
CPC ............ *A61K 31/575* (2013.01); *A61K 9/0031* (2013.01); *A61K 9/2054* (2013.01); *A61K 9/2866* (2013.01); *A61K 35/413* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,330,761 A * | 7/1994 | Baichwal ...................... 424/469 |
| 5,415,872 A | 5/1995 | Sipos |
| 5,908,830 A | 6/1999 | Smith et al. |
| 6,060,465 A * | 5/2000 | Miljkovic et al. ............. 514/169 |
| 6,303,661 B1 | 10/2001 | Demuth et al. |
| 6,309,663 B1 | 10/2001 | Patel et al. |
| 6,890,898 B2 | 5/2005 | Bachovchin et al. |
| 8,232,281 B2 * | 7/2012 | Dugi et al. ............... 514/263.21 |
| 8,318,663 B2 | 11/2012 | Young et al. |
| 8,680,085 B2 * | 3/2014 | Szewczyk ............ A61K 9/0031 514/182 |
| 2003/0139434 A1 | 7/2003 | Balkan et al. |
| 2003/0219472 A1 | 11/2003 | Pauletti et al. |
| 2004/0122033 A1 | 6/2004 | Nargund et al. |
| 2005/0009805 A1 | 1/2005 | Sasahara et al. |
| 2006/0193895 A1 | 8/2006 | Miura |
| 2008/0031968 A1 | 2/2008 | Bianco et al. |
| 2008/0145453 A1 | 6/2008 | Lopez et al. |
| 2008/0221161 A1 | 9/2008 | Pinkerton et al. |
| 2010/0130426 A1 | 5/2010 | Young et al. |
| 2013/0102581 A1 | 4/2013 | Szewczyk |

FOREIGN PATENT DOCUMENTS

| | | |
|---|---|---|
| EP | 0509335 A1 | 10/1992 |
| EP | 1273659 A1 | 1/2003 |
| EP | 1347052 A1 | 9/2003 |
| JP | S63-96138 | 4/1988 |
| JP | 2000-026300 | 1/2000 |
| JP | 2005-097216 A | 4/2005 |
| KR | 970005178 B1 | 12/1993 |
| WO | WO 00-62810 A1 | 10/2000 |
| WO | WO 02-08211 | 1/2002 |
| WO | WO 2006-031931 | 3/2006 |
| WO | WO 2006-057637 A1 | 6/2006 |
| WO | WO 2006-116814 A1 | 11/2006 |
| WO | WO 2007-095174 | 8/2007 |
| WO | WO 2008-002573 | 1/2008 |
| WO | WO 2008-058631 | 5/2008 |
| WO | WO 2008-067219 | 6/2008 |
| WO | WO 2008-091540 | 7/2008 |
| WO | WO 2010-059853 | 5/2010 |
| WO | WO2010-081079 | 7/2010 |
| WO | WO2011-038014 | 3/2011 |

OTHER PUBLICATIONS

Ostlund et al. 2003. Am. J. Clin. Nutr.77:1385.*
Al-Masri et al. 2009. J. Enzyme Inhib. Med. Chem. 24:1061-6.*
Saleem et al. 2014. J. Ethnopharm. 156:26-32.*
Lee et al. 1999. Int J. Pharmaceutics 188:71-80.*
Tomei et al. 2003. Biol. Pharm. Bull. 26:899-901.*
Lee et al. 1999. Int. J. Pharmaceutics. 188:71-80.*
PCT/US2009/65587 International Preliminary Report on Patentability dated Jun. 9, 2011.
Adrian, T.E. et al., "Deoxycholate is an important releaser of peptide YY and enteroglucagon from the human colon," Gut 1993; vol. 34, p. 1219-1224.
Balas, et al., "The Dipeptidyl Peptidase IV Inhibitor Vildagliptin Suppresses Endogenous Glucose Production and Enhances Islet Function after Single-Dose Administration in Type 2 Diabetic Patients," The Journal of Clinical Endocrinology & Metabolism, 2007, vol. 92, No. 4, p. 1249-1255.

(Continued)

*Primary Examiner* — Shulamith H Shafer
(74) *Attorney, Agent, or Firm* — Wilson Sonsini Goodrich & Rosati

(57) ABSTRACT

Provided herein are methods and compositions for treating metabolic diseases and conditions associated with metabolic diseases.

11 Claims, 12 Drawing Sheets

(56) References Cited

OTHER PUBLICATIONS

Chen et al., "Liver receptor homologue-1 mediates species and cell line specific bile acid dependent negative feedback regulation of the apical sodium-dependent bile acid transporter," JBC 278: 19909-19916 (2003).
Crosignani et al., "Clinical pharrnacokinetics of therapeutic bile acids," Clin. Pharmacokinet. 30: 333-358 (1996).
Dumoulin, V., et al., "Peptide YY, Glucagon-Like Peptide-1, and Neurotensin Responses to Luminal Factors in the Isolated Vascularly Perfused Rat Ileum," Endocrinology, 1998, vol. 139, No. 9, p. 3780-3786.
El-Shattawy et al., "Effectiveness of rectal insulin suppositories containing sodium cholate in normal and insulin dependent diabetic subjects," Pharmaceutical Res 8: S157 (1991).
Enhsen et al., "Bile acids in drug discovery," Drug Discov. Today 3: 409-418 (1998).
EP09829741 Extended Search Report dated Nov. 22, 2012.
GB0920703.6 Search Report mailed Mar. 10, 2010.
Genet et al., "Structure-activity relationship study of betulinic acid, a novel and selective TGR5 agonist and its synthetic derivatives: potential impact in diabetes," J. Med. Chem. 53: 178-190 (2010).
Hosny et al., "Relative hypoglycemia of rectal insulin suppositories containing deoxycholic acid, sodium taurocholate, polycarbophil and their combinations in diabetic rabbits," Drug Dev. Ind. Pharm. 25: 745-752 (1999).
Hosny et al., "Effect of different bile salts on the relative hypoglycemia of witepsol W35 suppositories containing insulin in diabetic beagle dogs," Drug. Dev. Ind. Pharm. 27: 837-845 (2001).
Hosny et al., "Evaluation of efficiency of insulin suppository formulations containing sodium salicylate or sodium cholate in insulin dependent diabetic patients," Bollettino Chimico Farmceutico 142: 361-366 (2003).
Katsuma et al., "Bile acids promote glucagon-like peptide-1 secretion through TGR5 in a murine enteroendocrine cell line STC-1," Biochem Biophy Res Commun. 329: 386-390 (2005).
Kawamata et al., "A G protein coupled receptor responsive to bile acid," JBC 278: 9435-9440 (2003).
Lim et al., "Glucagon-like peptide 1 secretion by the L-Cell," Diabetes 55: S70-S77 (2006).
Macchiarulo et al., "Molecular field analysis and 3D-quantitiative structure activity relationship study (MFA 3D-QSAR) unveil novel features of bile acid recognition at TGR5," J. Chem. Inf. Model. 48:1792-1801 (2008).
Mitsuhiro Watanabe, "Bile acid and diabetes," Functional Food, Apr. 2008, vol. 2, No. 1, p. 57-63.
Mitsuyoshinamba, et al., "A new prevention and treatment of diabetes using GLP-1 related drugs," Magazine of Japanese Society of Gastroenterology, 2005, vol. 102, No. 11, p. 1398-1404.
Onaga et al., "Multiple regulation of peptide YY secretion in the digestive tract," Peptides 17: 279-290 (2002).
PCT/US09/65587 Search Report mailed Jul. 27, 2010.
PCT/US2011/038251 International Search Report mailed Jan. 19, 2012.
Pellicciari et al., "Nongenomic actions of bile acids. Synthesis and preliminary characterization of 23- and 6,23-alkyl-substituted bile acid derivatives as selective modulators for the G-protein coupled receptor TGR5," J.Med.Chem. 50: 4265-4268 (2007).
Raun, K. et al., "Liraglutide, a Long-Action Glucagon-Like Peptide-1 Analog, Reduces Body Weight and Food Intake in Obese Candy-Fed Rats, Whereas a Dipeptidyl Peptidase-IV Inhibitor, Vildagliptin, Does No," Diabetes, vol. 56, Jan. 2007, p. 8-15.
Reimann et al., "Signaling mechanism underlying the release of glucagon-like peptide 1," Diabetes 55(Suppl.2): S78-S85 (2006).
Sato et al., "Anti-hyperglycemic activity of a TGR5 agonist isolated form *Olea europaea*," Biochem. Biophys. Res. Commun. 362: 793-798 (2007).
Sato et al., "Novel potent and selective bile acid derivatives as TGR5 agonists: biological screening, structure-activity relationships, and molecular modeling studies," J. Med. Chem. 51: 1831-1841 (2008).
Spangeus et al., "Large intestinal endocrine cells in non-obese diabetic mice," J. Diab. Comp. 12: 321-327 (1998).
Tenjarla et al., "Release of 5-Aminosaticylate from and MMX mesalamine tablet during transit through a simulated gastrointestinal tract system," Advances in Therapy 23: 826-940 (2007).
Tozaki et al., "Chitosan capsules for colon-specific drug delivery: improvement of insulin absorption from the rat colon," J Pharm Sci 86: 1016-1021 (1997).
U.S. Appl. No. 12/623,977 Office Action mailed Jan. 31, 2012.
U.S. Appl. No. 12/623,977 Office Action mailed Sep. 25, 2012.
U.S. Appl. No. 12/623,977 Office Action mailed Apr. 26, 2013.
U.S. Appl. No. 12/624,345 Office Action mailed May 26, 2011.
U.S. Appl. No. 12/624,345 Office Action mailed Nov. 16, 2011.
U.S. Appl. No. 12/624,345 Office Action mailed Feb. 15, 2012.
U.S. Appl. No. 12/624,345 Notice of Allowance mailed Sep. 21, 2012.
Wu et al., "Expression of bitter taste receptors of the T2R family in the gastrointestinal tract and enteroendocrine STC-1 cells," PNAS 99: 2392-2397 (2009).
Wynne et al., "Appetite Control," J. Endocrinol. 184: 291-318 (2005).
Yamamoto et al., "Colon-specific delivery of peptide drugs and anti-inflammatory drugs using chitosan capsules," Sciences Techniqus et Pratiques 10: 23-34 (2000).
Ziv et al., "Bile salts promote the absorption of insulin from the rat colon," Life Sci. 29: 803-809 (1981).
Martinez et al. Different bile acids exhibit distinct biological effects: the tumor promoter deoxycholic acid induces apoptosis and the chemopreventive agent ursodeoxycholic acid inhibits cell proliferation. Nutr Canc 31(2):111-118 (1998).

\* cited by examiner

Glucose response to taurocholic acid

L-cell activation anorexigenic hormones

METHODS OF TREATING DIABETES OR OBESITY USING BILE ACIDS, BILE SALTS, AND MIMICS THEREOF

CROSS-REFERENCE

This application is a continuation of U.S. application Ser. No. 12/624,345, filed Nov. 23, 2009, which issued as U.S. Pat. No. 8,318,663 on Nov. 27, 2012, and claims the benefit of U.S. Provisional Application Nos. 61/118,324, filed Nov. 26, 2008, and 61/255,211, filed Oct. 27, 2009. The entire contents of each of the above-applications are incorporated herein by reference.

BACKGROUND OF THE INVENTION

Obesity is a medical condition affecting numerous humans in a number of countries throughout the world, and is associated with or induces other diseases or conditions. In particular, obesity is a serious risk factor for diseases and conditions such as diabetes, hypertension, gallbladder disease, cancer, polycystic ovary disease and arteriosclerosis and can contribute to elevated levels of cholesterol in the blood. In addition, increased body weight due to obesity places a burden on joints causing arthritis, pain, and stiffness. Overeating and obesity have become a problem in the general population, consequently there is interest in losing weight, reducing weight, and/or maintaining a healthy body weight and lifestyle.

SUMMARY OF THE INVENTION

Provided in certain embodiments herein is a pharmaceutical composition comprising:
a. a therapeutically effective amount of an enteroendocrine peptide secretion enhancing agent;
b. an absorption inhibitor of the enteroendocrine peptide secretion enhancing agent; and
c. a carrier.

In some embodiments, the pharmaceutical composition is formulated for non-systemic rectal or colonic delivery of the enteroendocrine peptide secretion enhancing agent. In certain embodiments, the enteroendocrine peptide secretion enhancing agent is a bile acid, a bile salt, a bile acid mimic, a bile salt mimic, or a combination thereof. In some embodiments, the enteroendocrine peptide secretion enhancing agent is a glucagon-like peptide secretion enhancing agent, optionally in combination with a bile acid, a bile salt, a bile acid mimic, or a bile salt mimic. In certain embodiments, the glucagon-like peptide secretion enhancing agent is a glucagon-like peptide-1 (GLP-1) secretion enhancing agent or a glucagon-like peptide-2 (GLP-2) secretion enhancing agent, optionally in combination with a bile acid, a bile salt, a bile acid mimic, or a bile salt mimic. In some embodiments, the enteroendocrine peptide secretion enhancing agent is a pancreatic polypeptide-fold peptide secretion enhancing agent, optionally in combination with a bile acid, a bile salt, a bile acid mimic, or a bile salt mimic. In some embodiments, the pancreatic polypeptide-fold peptide secretion enhancing agent is a peptide YY (PYY) secretion enhancing agent.

In certain embodiments, the composition further comprises at least one of a cholesterol absorption inhibitor, a spreading agent or a wetting agent. In some embodiments, the absorption inhibitor is a mucoadhesive agent. In specific embodiments, the polymer having mucoadhesive properties is selected from methyl cellulose, polycarbophil, polyvinylpyrrolidone, sodium carboxymethyl cellulose, and combinations thereof. In some embodiments, the enteroendocrine peptide secretion enhancing agent is covalently linked to the absorption inhibitor.

In certain embodiments, the carrier is a rectally suitable carrier. In certain embodiments, any pharmaceutical composition described herein is formulated as a suppository, an enema solution, a rectal foam, or a rectal gel. In some embodiments, any pharmaceutical composition described herein comprises an orally suitable carrier. In certain embodiments, the pharmaceutical composition comprises an enteric coating.

In some embodiments, any composition described herein further comprises an enteroendocrine peptide.

Provided in certain embodiments herein is a method for treating a metabolic disease or a condition associated with a metabolic disease comprising administering to the lower ileum, the colon and/or the rectum of an individual in need thereof, a pharmaceutical composition comprising a therapeutically effective amount of an enteroendocrine peptide secretion enhancing agent. Provided in certain embodiments herein is a method for treating a metabolic disease or a condition associated with a metabolic disease comprising administering (e.g., orally or rectally administering) to an individual in need thereof, a pharmaceutical composition comprising a therapeutically effective amount of an enteroendocrine peptide secretion enhancing agent and a carrier. In some embodiments, administered is a pharmaceutical composition that further comprises an absorption inhibitor, wherein the absorption inhibitor inhibits the absorption of the enteroendocrine peptide secretion enhancing agent across the rectal or colonic mucosa. In some embodiments, the composition administered comprises an orally suitable carrier. In certain embodiments, the pharmaceutical composition is formulated for enteric delivery. In some embodiments, the pharmaceutical composition comprises an enteric coating.

Provided in certain embodiments herein is a method for treating obesity or diabetes comprising administering to the lower ileum, the colon and/or the rectum of an individual in need thereof, a pharmaceutical composition comprising a therapeutically effective amount of an enteroendocrine peptide secretion enhancing agent. Provided in some embodiments herein is a method for treating obesity or diabetes comprising administering (e.g., orally or rectally administering) to an individual in need thereof, a pharmaceutical composition comprising a therapeutically effective amount of an enteroendocrine peptide secretion enhancing agent and a carrier. In some embodiments, administered is a pharmaceutical composition that further comprises an absorption inhibitor, wherein the absorption inhibitor inhibits the absorption of the enteroendocrine peptide secretion enhancing agent across the rectal or colonic mucosa. In some embodiments, the composition administered comprises an orally suitable carrier. In certain embodiments, the pharmaceutical composition is formulated for enteric delivery. In some embodiments, the pharmaceutical composition comprises an enteric coating.

In some embodiments, administered according to a method described herein is a composition comprising a rectally suitable carrier. In some embodiments, the administered pharmaceutical composition is formulated as a suppository, an enema solution, a rectal foam, or a rectal gel.

In certain embodiments, a composition administered according to a method described herein comprises a enteroendocrine peptide secretion enhancing agent that is a bile acid, bile salt, bile acid mimic or bile salt mimic. In some embodiments, the enteroendocrine peptide secretion enhancing agent is a glucagon-like peptide secretion enhancing agent. In certain embodiments, the enteroendocrine peptide secretion enhancing agent is a glucagon-like peptide-1 (GLP-1) secretion enhancing agent or a glucagon-like peptide-2 (GLP-2) secretion enhancing agent. In some embodiments, the enteroendocrine peptide secretion enhancing agent is a pancreatic polypeptide-fold peptide secretion enhancing agent. In specific embodiments, the enteroendocrine peptide secretion enhancing agent is a peptide YY (PYY) secretion enhancing agent. In some embodiments, a composition administered according to a method described herein comprises any one or more of the enteroendocrine peptide secretion enhancing agents described herein.

In some embodiments, the composition administered comprises at least one of a cholesterol absorption inhibitor, a spreading agent or a wetting agent. In some embodiments, the absorption inhibitor is a mucoadhesive agent (e.g., a mucoadhesive polymer). In certain embodiments, the mucoadhesive agent is selected from methyl cellulose, polycarbophil, polyvinylpyrrolidone, sodium carboxymethyl cellulose, and combinations thereof. In some embodiments, a pharmaceutical composition administered further comprises an enteroendocrine peptide.

In certain embodiments, the enteroendocrine peptide secretion enhancing agent is delivered to and/or the pharmaceutical composition comprising the same is administered to the colon, rectum or to the colon and rectum of the individual.

In some embodiments, the condition treated is weight gain, appetite, food intake, impaired glucose tolerance, a glucose metabolic disorder, or insulin resistance. In some embodiments, the metabolic disease is obesity, diabetes or a combination thereof.

Provided in some embodiments herein is a kit comprising any composition described herein (e.g., a pharmaceutical composition formulated for rectal administration) and a device for localized delivery within the rectum or colon. In certain embodiments, the device is a syringe, bag, or a pressurized container.

Provided in some embodiments herein is the use of any pharmaceutical composition described herein in the manufacture of a medicament for the treatment of a metabolic disorder or a condition associated with a metabolic disorder. In some embodiments, the condition associated with a metabolic disorder is weight gain, appetite, food intake, impaired glucose tolerance, a glucose metabolic disorder, or insulin resistance. In specific embodiments, the metabolic disease is obesity, diabetes or a combination thereof.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 1 illustrates the response of enteroendocrine peptides to administration of bile salts.

DETAILED DESCRIPTION OF THE INVENTION

Figure 1A:
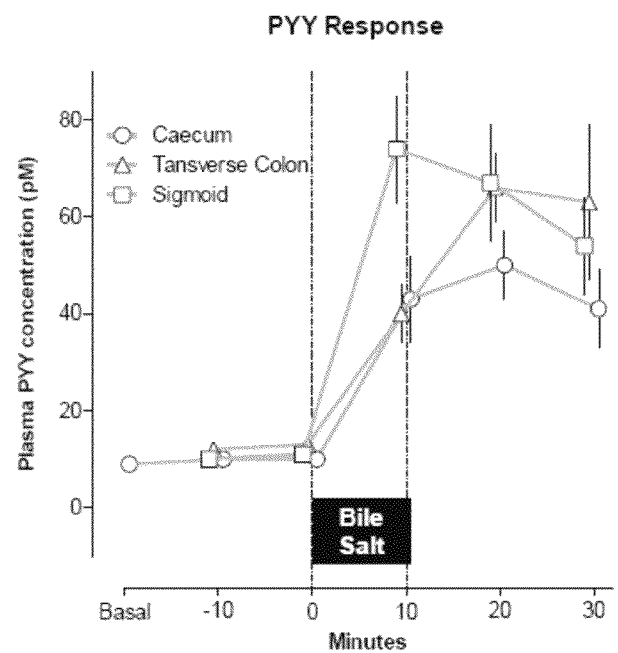
FIG. 1A illustrates the plasma PYY concentrations in the caecum, transverse colon, and sigmoid as a result of bile salt administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

DEFINITIONS

The term "bile acid," as used herein, includes steroid acids (and/or the carboxylate anion thereof), and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocolate, and the like. Taurocholic acid and/or taurocholate are referred to herein as TCA. Any reference to a bile acid used herein includes reference to a bile acid, one and only one bile acid, one or more bile acids, or to at least one bile acid. Therefore, the terms "bile acid," "bile salt," "bile acid/salt," "bile acids," "bile salts," and "bile acids/salts" are, unless otherwise indicated, utilized interchangeably herein. Any reference to a bile acid used herein includes reference to a bile acid or a salt thereof. Furthermore, pharmaceutically acceptable bile acid esters are optionally utilized as the "bile acids" described herein, e.g., bile acids conjugated to an amino acid (e.g., glycine or taurine). Other bile acid esters include, e.g., substituted or unsubstituted alkyl ester, substituted or unsubstituted heteroalkyl esters, substituted or unsubstituted aryl esters, substituted or unsubstituted heteroaryl esters, or the like. For example, the term "bile acid" includes cholic acid conjugated with either glycine or taurine: glycocholate and taurocholate, respectively (and salts thereof). Any reference to a bile acid used herein includes reference to an identical compound naturally or synthetically prepared. Furthermore, it is to be understood that any singular reference to a component (bile acid or otherwise) used herein includes reference to one and only one, one or more, or at least one of such components. Similarly, any plural reference to a component used herein includes reference to one and only one, one or more, or at least one of such components, unless otherwise noted.

The term "colon," as used herein, includes the cecum, ascending colon, hepatic flexure, splenic flexure, descending colon, and sigmoid.

The term "composition," as used herein includes the disclosure of both a composition and a composition administered in a method as described herein. Furthermore, in some embodiments, the composition of the present invention is or comprises a "formulation," an oral dosage form or a rectal dosage form as described herein.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic. Furthermore, the alkyl moiety, whether saturated or unsaturated, may comprise branched, straight chain, and/or cyclic portions. Depending on the structure, an alkyl group can be a monoradical or a diradical (i.e., an alkylene group). A "heteroalkyl" group is as described for "alkyl" with at least one of the C atoms thereof substituted with an N, S, or O atom. The "heteroalkyl" group may comprise linear, branched, and/or cyclic portions. In certain embodiments, a "lower alkyl" is an alkyl group with 1-6 carbon atoms (i.e., a $C_1$-$C_6$ alkyl group). In specific instances, the "lower alkyl" may be straight chained or branched.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Illustrative examples of cycloalkyl groups include the following moieties:

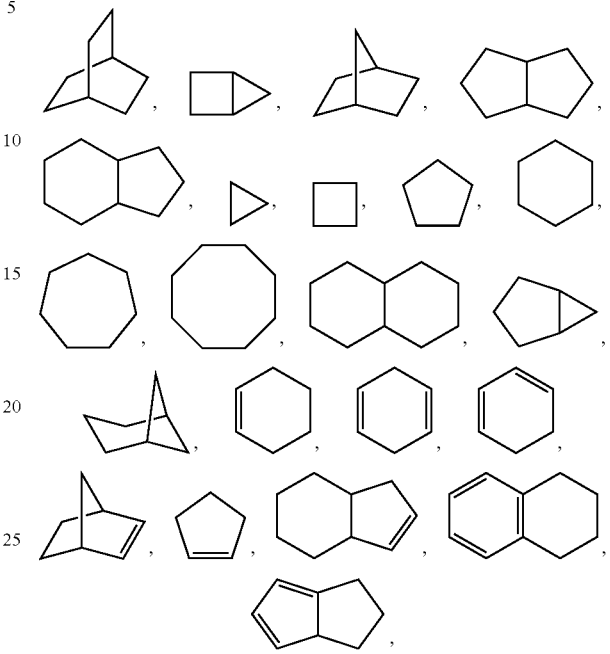

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

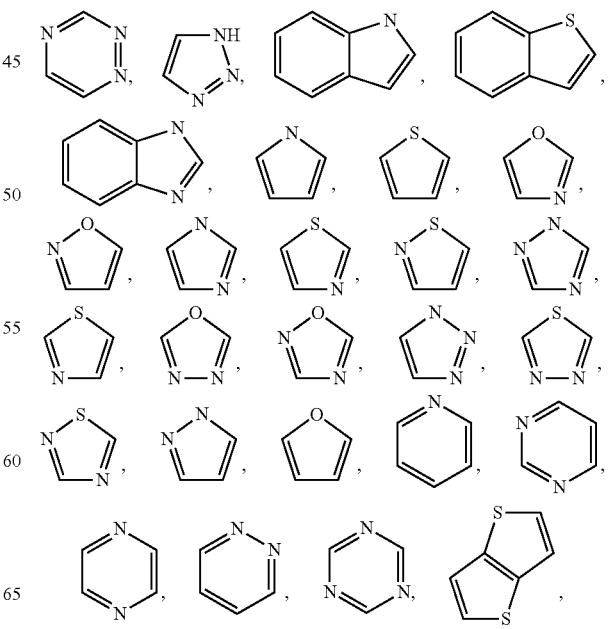

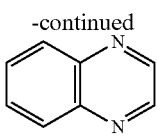

and the like. Depending on the structure, a heteroaryl group can be a monoradical or a diradical (i.e., a heteroarylene group).

A "heterocycloalkyl" group refers to a cycloalkyl group that includes at least one ring atom that is not a carbon, i.e. at least one ring atom is a heteroatom selected from nitrogen, oxygen and sulfur. The heterocycloalkyl radicals may be fused with an aryl or heteroaryl. Illustrative examples of heterocycloalkyl groups, also referred to as non-aromatic heterocycles, include:

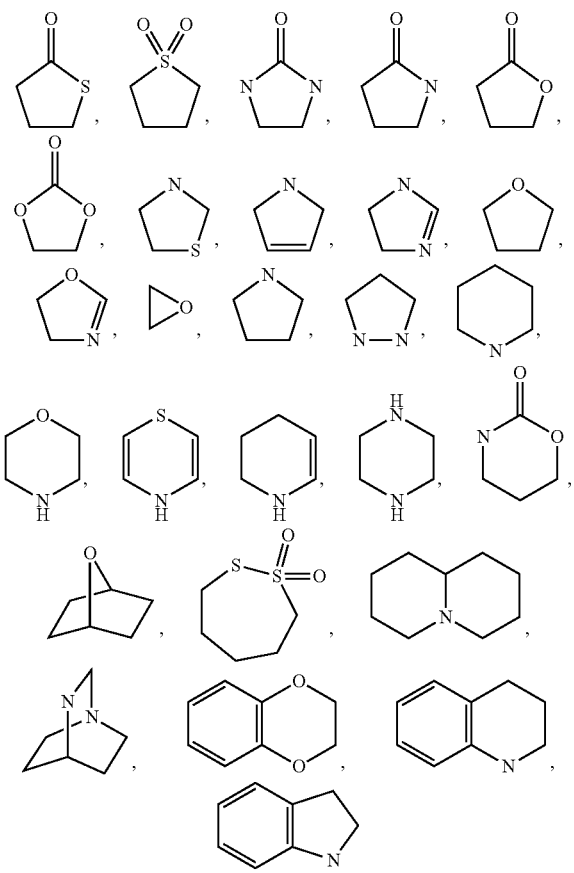

and the like. The term heteroalicyclic also includes all ring forms of the carbohydrates, including but not limited to the monosaccharides, the disaccharides and the oligosaccharides. Heterocycloalkyls have from 2 to 10 carbons in the ring. A "lower heterocycloalkyl" has 2 to 8 ring carbon atoms. It is understood that when referring to the number of carbon atoms in a heterocycloalkyl, the number of carbon atoms in the heterocycloalkyl is not the same at the total number of atoms (including the heteroatoms) that make up the heterocycloalkyl (i.e skeletal atoms of the heterocycloalkyl ring).

The term "modulate," as used herein refers to having some affect on (e.g., increasing, enhancing or maintaining a certain level).

The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$-fluoroalkyl, and amino, including $C_1$-$C_6$alkylamino, and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art and may be found in references such as Greene and Wuts, above. In some embodiments, alkyl groups described herein are optionally substituted with an O that is connected to two adjacent carbon atoms (i.e., forming an epoxide).

The term "therapeutically effective amount" or an "effective amount" as used herein, refers to a sufficient amount of a therapeutically active agent to provide a desired effect in a subject or individual. In some embodiments, a "therapeutically effective amount" or an "effective amount" of an enteroendocrine peptide secretion enhancing agent refers to a sufficient amount of the enteroendocrine peptide secretion enhancing agent to a treat a metabolic disorder in a subject or individual. In some embodiments, a "therapeutically effective amount" or an "effective amount" of an enteroendocrine peptide secretion enhancing agent refers to a sufficient amount of the enteroendocrine peptide secretion enhancing agent to increase the secretion of enteroendocrine peptide(s) in a subject or individual. In specific embodiments, the "therapeutically effective amount" is an amount that when delivered to the colon or rectum it produces an anorectal response (e.g., it increase the secretion of enteroendocrine peptide(s) in the rectum and/or colon, particularly in the L-cells, of an individual). In some embodiments, a "therapeutically effective amount" or an "effective amount" of an enteroendocrine peptide secretion enhancing agent refers to a sufficient amount of the enteroendocrine peptide secretion enhancing agent to decrease hunger in a subject, to curb appetite in a subject and/or decrease the food intake of a subject or individual.

Enteroendocrine Peptide Secretion

L-Cells

L-cells are scattered throughout the epithelial layer of the gut from the duodenum to the rectum, with the highest numbers occurring in the ileum, colon, and rectum. They are characterized by an open-cell morphology, with apical microvilli facing into the gut lumen and secretory vesicles located adjacent to the basolateral membrane, and are therefore in direct contact with nutrients in the intestinal lumen. Furthermore, L-cells are located in close proximity to both neurons and the microvasculature of the intestine, thereby allowing the L-cell to be affected by both neural and hormonal signals. As well as Glucagon-Like Peptide 1 (GLP-1) and Glucagon-Like Peptide 2 (GLP-2), L-cells also secrete the anorexigenic hormone, peptide YY (PYY), and glutamate. The cells are just one member of a much larger family of enteroendocrine cells that secrete a range of hormones, including ghrelin, GIP, cholecystokinin, somatostatin, and secretin, which are involved in the local coordination of gut physiology, as well as in playing wider roles in the control of insulin release and appetite. L-cells are unevenly distributed in the gastrointestinal tract, within higher concentrations in the distal portion of the gastrointestinal tract (e.g., in the distal ileum, colon and rectum).

Proglucagon Products

The proglucagon gene product is expressed in the L-cells of the small intestine, in α-cells of the pancreas and in the central nervous system. Tissue-specific expression of isoforms of the enzyme prohormone convertase directs post-translational synthesis of specific proglucagon-derived peptides in the L-cell and α-cell. Specifically, cleavage of proglucagon by prohormone convertase ⅓, which is expressed in the L-cell, forms GLP-1 and GLP-2, as well as the glucagon-containing peptides, glicentin and oxyntomodulin. In contrast, α-cell expression of prohormone convertase 2 forms glucagon, glicentin-related pancreatic peptide, and the major proglucagon fragment, which contains within its sequence both the GLP-1 and GLP-2 sequences.

Glucagon-like peptide 1 (GLP-1) is an intestinal hormone that effects in the regulation of glycemia, stimulating glucose-dependent insulin secretion, proinsulin gene expression, and B-cell proliferative and anti-apoptotic pathways, as well as inhibiting glucagon release, gastric emptying, and food intake. The anorexigenic effect of GLP-1 is mediated by GLP-1 receptors which are present in both the NTS and hypothalamus, and in the pancreas, lung, brain, kidney, gastrointestinal tract and heart. Reduced secretion of GLP-1 contributes to the pathogenesis of obesity and enhanced/or normal secretion restores satiety.

The primary physiological stimulus of GLP-1 secretion from L-cells is ingestion of carbohydrates, luminal glucose (not systemic glucose) fat, and protein. Protein hydrolysate are also potent triggers of GLP-1 release, and certain amino acids such as, but not limited to, alanine, serine, glutamine, asparagine, and glycine stimulate GLP-1 release. Within the fat group, the long-chain unsaturated fatty acid and short-chain fatty acid subgroups are potent triggers of GLP-1 release, while the short-chain fatty acids also stimulate peptide YY release. In addition to luminal nutrients, intestinal peptides, neurotransmitters, as well as systemic hormones, modulate GLP-1 secretion. Such intestinal peptides include, but are not limited to, somatostatin (forms SS14 and SS28), and such neurotransmitters include, but are not limited to, acetylcholine and γ-aminobutyric acid (GABA) (both of which enhance GLP-1 release), and α- and β-adrenergic agonists, (which respectively inhibit and/or stimulate GLP-1 secretion from L-cells). Peripheral hormones that participate in energy homeostasis, such as the adipocyte hormone leptin, also stimulate GLP-1 release. Other GLP-1 secretegoues include bile acids/salts, insulin, gastrin-releasing peptide (GRP), several gut peptides including, but not limited to, Gastric Inhibitory Polypeptide (GIP) and calcitonin gene-related protein (CGRP). CGRP is a peptide found throughout the enteric nervous system. Thus, GLP-1 secretagogues include, but are not limited to, nutrients, neurotransmitters, neuropeptides, intestinal peptide, peripheral hormones, and bile acis/salts.

Within about 15 minutes of food ingestion the circulating GLP-1 levels increase and remain elevated for up to 3 hours, depending on the composition of the meal. Circulating GLP-1 exists in two equipotent forms, GLP-1$^{7\text{-}36NH2}$ and GLP-1$^{7\text{-}37}$, with GLP-1$^{7\text{-}36NH2}$ being the predominant form. Secreted GLP-1 is rapidly degraded by the ubiquitous enzyme dipeptidyl peptidase-4 (DPP-4), resulting in an extremely short half-life for GLP-1 of about 30 seconds to about 2 minutes. Therefore, levels of circulating GLP-1 are maintained by inhibiting DPP-4 activity, or alternatively, by enhancing GLP-1 secretion.

Figure 9:
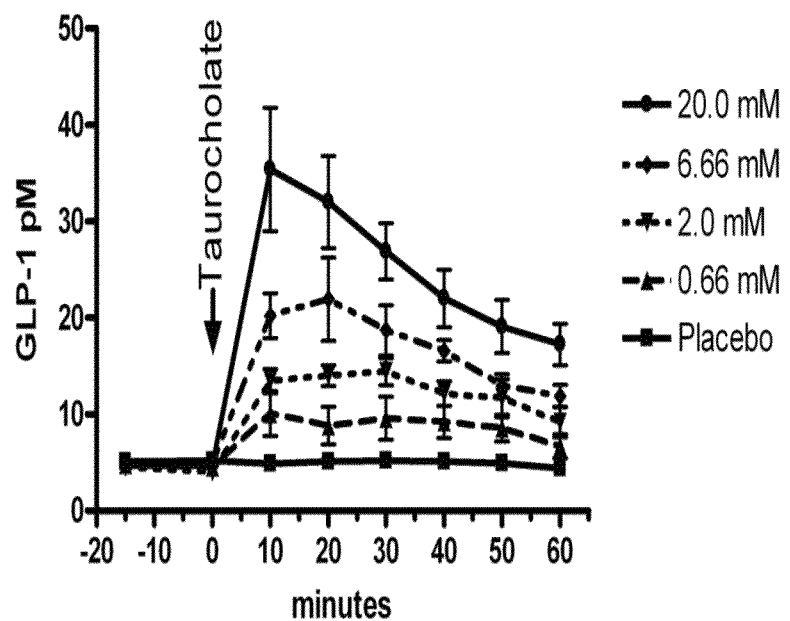
FIG. 9 illustrates the acute release of GLP-1 in response to administration of bile acids in obese human diabetics.

In some embodiments, provided herein is a method of increasing circulating GLP (e.g., GLP-1) levels by administering to the distal gastrointestinal tract (e.g., distal ileum, colon and/or rectum) an effective amount of an enteroendocrine peptide secretion enhancing agent (e.g., a bile acid). In certain embodiments, the method is included in a method of treating a metabolic disorder. In some embodiments, the method is included in a method of treating obesity or diabetes. FIG. 9 illustrates the increase of circulating GLP-1 levels following rectal administration of an enteroendocrine peptide secretion enhancing agent (e.g., a bile acid). FIG. 9 illustrates the increase of circulating GLP-1 levels following rectal administration of taurocholic acid.

Pancreatic Polypeptide (PP)-Fold Peptides

The Pancreatic Polypeptide (PP)-fold peptides include Peptide YY (PYY), Pancreatic Polypeptide (PP) and Neuropeptide Y (NPY), which all share sequence homology and contain several tyrosine residues. They have a common tertiary structure which consists of an α-helix and polyproline helix, connected by a B-turn, resulting in a characteristic U-shaped peptide, the PP-fold.

Neuropeptide Y (NPY) is one of the most abundant neurotransmitters in the brain. Hypothalamic levels of NPY reflect the body's nutritional status, wherein the levels of hypothalamic NPY mRNA and NPY release increase with fasting and decrease after feeding.

Pancreatic Polypeptide (PP) is produced by cells at the periphery of the islets of the endocrine pancreas, and to a lesser extent in the exocrine pancreas, colon and rectum. The release of PP is biphasic and occurs in proportion to the number of calories ingested, with the levels remaining elevated for up to 6 hours post-prandially. The circulating levels of PP are increased by gastric distension, ghrelin, motilin and secretin and reduced by somatostatin. In addition, circulating PP exhibits a diurnal rhythm, with levels low in the early hours of the morning and highest in the evening. The levels of PP have been found to reflect long-term energy stores, with lower levels and reduced second phase of release in obese subjects, and higher levels in anorexic subjects. Circulating PP is unable to cross the blood-brain barrier, but exerts its anorectic effect by sending anorectic signals via brainstem pathways, hypothalamic neuropeptides and by modulating expression of other gut hormones such as ghrelin.

Figure 8:
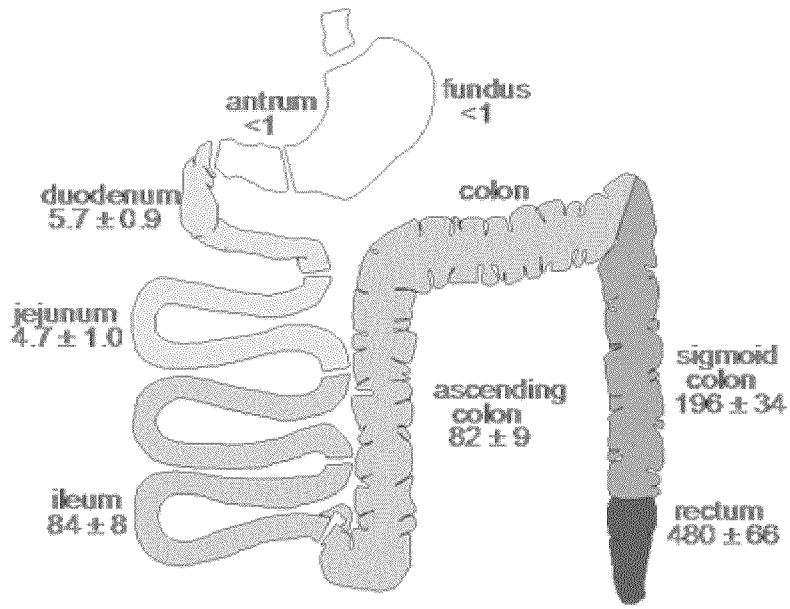
FIG. 8 illustrates the normal GI distribution of PYY (pmol/g).

Peptide YY (PYY) is secreted predominantly from the distal gastrointestinal tract, particularly the ileum, colon and rectum. FIG. 8 illustrates the concentration of PYY at various locations in the gastrointestinal tract. The L-cells of the intestine release PYY in proportion to the amount of calories ingested, and occurs before the nutrients reach the cells in the distal tract. Thus, release may be mediated via a neural reflex as well as direct contact with nutrients. Post-prandially, the circulating PYY levels rise rapidly to a plateau after 1-2 hours and remain elevated for up to 6 hours. The levels of PYY are also influenced by meal composition, with higher levels obtained following fat intake relative to carbohydrate or protein intake. Other signals, such as gastric acid, CCK and luminal bile salts, insulin-like growth factor 1, bombesin and calcitonin-gene-related peptide increase PYY levels, whereas gastric distension has no effect, and levels are reduced by GLP-1. The N-terminal of circulating PYY allows it to cross the blood-brain barrier.

Figure 10:
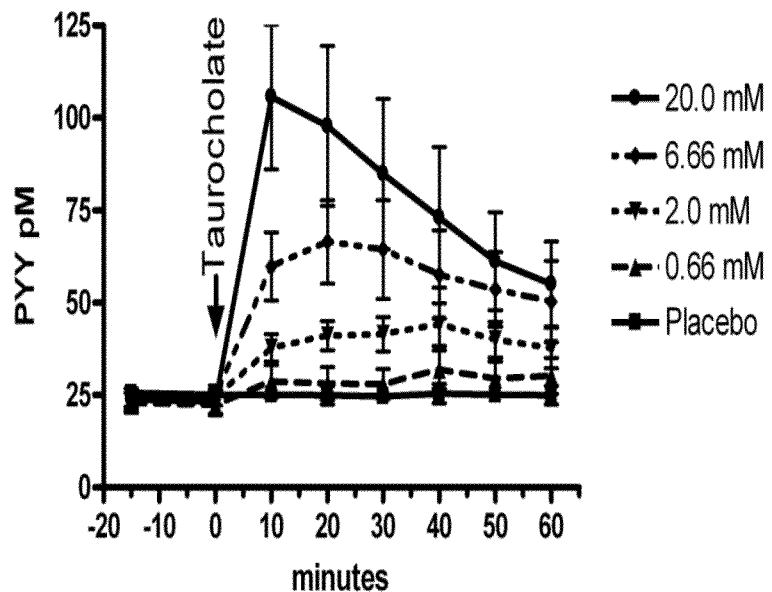
FIG. 10 illustrates the acute release of PYY in response to administration of bile acids in obese human diabetics.

In some embodiments, provided herein is a method of increasing circulating PYY levels by administering to the distal gastrointestinal tract (e.g., distal ileum, colon and/or rectum) an effective amount of an enteroendocrine peptide secretion enhancing agent (e.g., a bile acid). In certain embodiments, the method is included in a method of treating a metabolic disorder. In some embodiments, the method is included in a method of treating obesity or diabetes. FIG. 10 illustrates the increase of circulating PYY levels following rectal administration of an enteroendocrine peptide secretion enhancing agent (e.g., a bile acid).

Enteroendocrine Peptide Secretion Enhanced Treatment

Intravenous administration of GLP-1 decreases food intake in both lean and obese individuals in a dose-dependent manner, although the effect is small when infusions achieve post-prandial circulating levels. In addition, obese subjects given subcutaneous GLP-1 prior to each meal, reduce their caloric intake. Thus, modulation/control of GLP-1 secretion restore satiety and controls appetite and food intake. Similarly, infusion of PP decreases appetite and food intake. Obese humans have a relatively low level of circulating PYY and a relative deficiency of post-prandial secretion of PYY. Administration of PYY causes a delay in gastric emptying, a delay in secretions from the pancreas and stomach, and increases the absorption of fluids and electrolytes from the ileum after a meal. In addition, intravenous administration of PYY decreases appetite, inhibits food intake and reduces weight gain.

Appetite, weight gain and food intake are controlled by the circulating or systemic levels of GLP-1, PYY and PP. The methods and composition described herein use, by way of non-limiting example, the administration of bile acids/salts and bile acids/salts mimics to modulate (e.g., increase) the circulating levels of GLP-1, PYY and PP. In certain embodiments of the present invention, such administration decreases food intake and weight gain while suppressing appetite.

Bile Acid

Bile contains water, electrolytes and a numerous organic molecules including bile acids, cholesterol, phospholipids and bilirubin. Bile is secreted from the liver and stored in the gall bladder, and upon gall bladder contraction, due to ingestion of a fatty meal, bile passes through the bile duct into the intestine. Bile acids are critical for digestion and absorption of fats and fat-soluble vitamins in the small intestine. Adult humans produce 400 to 800 mL of bile daily. The secretion of bile can be considered to occur in two stages. Initially, hepatocytes secrete bile into canaliculi, from which it flows into bile ducts and this hepatic bile contains large quantities of bile acids, cholesterol and other organic molecules. Then, as bile flows through the bile ducts, it is modified by addition of a watery, bicarbonate-rich secretion from ductal epithelial cells. Bile is concentrated, typically five-fold, during storage in the gall bladder.

The flow of bile is lowest during fasting, and a majority of that is diverted into the gallbladder for concentration. When chyme from an ingested meal enters the small intestine, acid and partially digested fats and proteins stimulate secretion of cholecystokinin and secretin, both of which are important for secretion and flow of bile. Cholecystokinin (cholecysto=gallbladder and kinin=movement) is a hormone which stimulates contractions of the gallbladder and common bile duct, resulting in delivery of bile into the gut. The most potent stimulus for release of cholecystokinin is the presence of fat in the duodenum. Secretin is a hormone secreted in response to acid in the duodenum, and it simulates biliary duct cells to secrete bicarbonate and water, which expands the volume of bile and increases its flow out into the intestine.

Bile acids are derivatives of cholesterol. Cholesterol, ingested as part of the diet or derived from hepatic synthesis, are converted into bile acids in the hepatocyte. Examples of such bile acids include cholic and chenodeoxycholic acids, which are then conjugated to an amino acid (such as glycine or taurine) to yield the conjugated form that is actively secreted into cannaliculi. The most abundant of the bile salts in humans are cholate and deoxycholate, and they are normally conjugated with either glycine or taurine to give glycocholate or taurocholate respectively.

Free cholesterol is virtually insoluble in aqueous solutions, however in bile it is made soluble by the presence of bile acids and lipids. Hepatic synthesis of bile acids accounts for the majority of cholesterol breakdown in the body. In humans, roughly 500 mg of cholesterol are converted to bile acids and eliminated in bile every day. Therefore, secretion into bile is a major route for elimination of cholesterol. Large amounts of bile acids are secreted into the intestine every day, but only relatively small quantities are lost from the body. This is because approximately 95% of the bile acids delivered to the duodenum are absorbed back into blood within the ileum, by a process is known as "Enterohepatic Recirculation".

Venous blood from the ileum goes straight into the portal vein, and hence through the sinusoids of the liver. Hepatocytes extract bile acids very efficiently from sinusoidal blood, and little escapes the healthy liver into systemic circulation. Bile acids are then transported across the hepatocytes to be resecreted into canaliculi. The net effect of this enterohepatic recirculation is that each bile salt molecule is reused about 20 times, often two or three times during a single digestive phase. Bile biosynthesis represents the major metabolic fate of cholesterol, accounting for more than half of the approximate 800 mg/day of cholesterol that an average adult uses up in metabolic processes. In comparison, steroid hormone biosynthesis consumes only about 50 mg of cholesterol per day. Much more that 400 mg of bile salts is required and secreted into the intestine per day, and this is achieved by re-cycling the bile salts. Most of the bile salts secreted into the upper region of the small intestine are absorbed along with the dietary lipids that they emulsified at the lower end of the small intestine. They are separated from the dietary lipid and returned to the liver for re-use. Re-cycling thus enables 20-30 g of bile salts to be secreted into the small intestine each day.

Bile acids are amphipathic, with the cholesterol-derived portion containing both hydrophobic (lipid soluble) and polar (hydrophilic) moieties while the amino acid conjugate is generally polar and hydrophilic. This amphipathic nature enables bile acids to carry out two important functions: emulsification of lipid aggregates and solubilization and transport of lipids in an aqueous environment. Bile acids have detergent action on particles of dietary fat which causes fat globules to break down or to be emulsified. Emulsification is important since it greatly increases the surface area of fat available for digestion by lipases which cannot access the inside of lipid droplets. Furthermore, bile acids are lipid carriers and are able to solubilize many lipids by forming micelles and are critical for transport and absorption of the fat-soluble vitamins.

Pharmaceutical Compositions and Methods of Use

In some embodiments, compositions described herein are administered for delivery of enteroendocrine peptide secretion enhancing agents to a subject or individual. In certain embodiments, any compositions described herein are formulated for ileal, rectal and/or colonic delivery. In more specific embodiments, the composition is formulated for non-systemic or local delivery to the rectum and/or colon. It is to be understood that as used herein, delivery to the colon includes delivery to sigmoid colon, transverse colon, and/or ascending colon. In still more specific embodiments, the composition is formulated for non-systemic or local delivery to the rectum and/or colon is administered rectally. In other specific embodiments, the composition is formulated for non-systemic or local delivery to the rectum and/or colon is administered orally.

In some embodiments, provided herein is a composition comprising an enteroendocrine peptide secretion enhancing agent and, optionally, a pharmaceutically acceptable carrier for reducing food intake in an individual. In some embodiments, provided herein is a composition comprising an enteroendocrine peptide secretion enhancing agent and, optionally, a pharmaceutically acceptable carrier for reducing circulating glucose levels in an individual. In some embodiments, provided herein is a composition comprising an enteroendocrine peptide secretion enhancing agent and, optionally, a pharmaceutically acceptable carrier for increasing insulin levels in an individual. In specific embodiments, the composition is formulated for delivering the enteroendocrine peptide secretion enhancing agent to the distal gastrointestinal tract of the individual. Generally, a therapeutically effective amount of an enteroendocrine peptide secretion enhancing agent is provided.

In certain embodiments, the composition comprises an enteroendocrine peptide secretion enhancing agent and an absorption inhibitor. In specific embodiments, the absorption inhibitor is an inhibitor that inhibits the absorption of the (or at least one of the) specific enteroendocrine peptide secretion enhancing agent with which it is combined. In some embodiments, the composition comprises an enteroendocrine peptide secretion enhancing agent, an absorption inhibitor and a carrier (e.g., an orally suitable carrier or a rectally suitable carrier, depending on the mode of intended administration). In certain embodiments, the composition comprises an enteroendocrine peptide secretion enhancing agent, an absorption inhibitor, a carrier, and one or more of a cholesterol absorption inhibitor, an enteroendocrine peptide, a peptidase inhibitor, a spreading agent, and a wetting agent.

In certain embodiments enteroendocrine peptide secretion enhancing agents are selected from, by way of non-limiting example, bile acids, bile acid mimic and/or modified bile acids. In more specific embodiments, compositions described herein are formulated for non-systemic or local delivery of a bile acid, bile acid mimic and/or modified bile acid (as the active component or components) to the rectum and/or colon, including the sigmoid colon, transverse colon, and/or ascending colon. In certain embodiments, the compositions described herein are administered rectally for non-systemic or local delivery of the bile acid active component to the rectum and/or colon, including the sigmoid colon, transverse colon, and/or ascending colon. In other embodiments, the compositions described herein are administered orally for non-systemic delivery of the bile salt active component to the rectum and/or colon, including the sigmoid colon, transverse colon, and/or ascending colon. In specific embodiments, compositions formulated for oral administration are, by way of non-limiting example, enterically coated or formulated oral dosage forms, such as, tablets and/or capsules. It is to be understood that the terms "subject" and "individual" are utilized interchangeably herein and include, e.g., humans and human patients in need of treatment.

Enteroendocrine Peptide Enhancing Agents

In some embodiments, enteroendocrine peptide enhancing agents provided herein include, by way of non-limiting example, enteroendocrine peptide secretion (e.g., of the L-cells) enhancing agents, inhibitors of degradation of enteroendocrine peptides (e.g., of the L-cells), or combinations thereof.

In certain embodiments, the enteroendocrine peptide secretion enhancing agents used in the methods and compositions described herein include, by way of non-limiting example, a steroid acid or a nutrient. In specific embodiments, the steroid acid or nutrient described herein is a steroid acid or nutrient that enhances the secretion of an enteroendocrine peptide. In specific embodiments, the steroid acid is an oxidize cholesterol acid. In some embodiments, an enteroendocrine peptide secretion enhancing agent, bile acid, or bile acid mimic used in any composition or method described herein is a compound of Formula I:

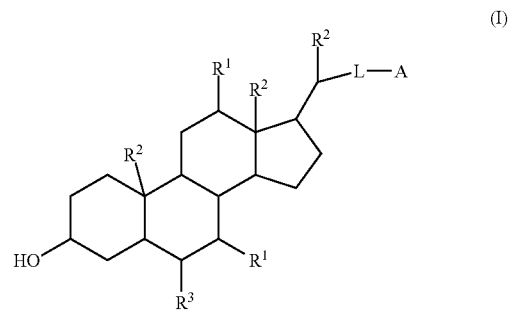

(I)

In certain embodiments, each $R^1$ is independently H, OH, O-lower alkyl (e.g., $OCH_3$, or OEt). In some embodiments, each $R^1$ is independently H, OH, lower (e.g., $C_1$-$C_6$ or $C_1$-$C_3$) alkyl, or lower (e.g., $C_1$-$C_6$ or $C_1$-$C_3$) heteroalkyl. In certain embodiments, L is a substituted or unsubstituted alkyl or substituted or unsubstituted heteroalkyl. In some embodiments, $R^2$ is H, OH, lower alkyl, or lower heteroalkyl (e.g., OMe). In certain embodiments, $R^3$ is H, OH, G-lower alkyl, lower alkyl, or lower heteroalkyl (e.g., OMe). In some embodiments, A is $COOR^4$, $S(O)_nR^4$, or $OR^5$. In certain embodiments, $R^4$ is H, an anion, a pharmaceutically acceptable cation (e.g., an alkali metal cation, alkaline earth metal cation, or any other pharmaceutically acceptable cation) substituted or unsubstituted alkyl, substituted or unsubstituted heteroalkyl, substituted or unsubstituted aryl, substituted or unsubstituted heteroaryl, an amino acid, or the like; and n is 1-3. Each $R^5$ is independently selected from lower alkyl and H.

In specific embodiments, L is unsubstituted branched or straight chain alkyl. In more specific embodiments, L is unsubstituted branched or straight chain lower alkyl. In some embodiments, L is $(CR^5{}_2)_m$—$CONR^5$—$(CR^5{}_2)_p$. Each m is 1-6 and n is 1-6. In specific embodiments, m is 2 and n is 1. In other specific embodiments, m is 2 and n is 2. In certain embodiments, A is COOH or COO—. In some embodiments, A is $SO_3H$ or $SO_3$—.

In specific embodiments, the compound of Formula I has a structure represented by Figure (Ia):

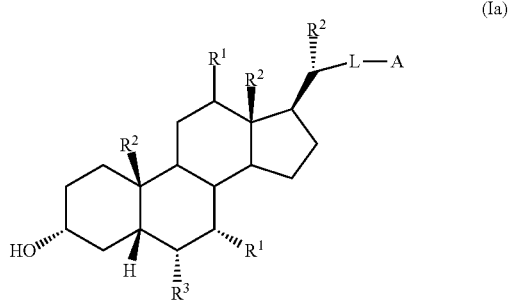

(Ia)

In some embodiments, bile acid mimics include, by way of non-limiting example, 6-methyl-2-oxo-4-thiophen-2-yl-1,2,3,4-tetrahydro-phyrimidine-5-carboxylic acid benzyl ester (or TGR5-binding analogs thereof), oleanolic acid (or TGR5-binding analogs thereof), or the like.

Figure 1B:
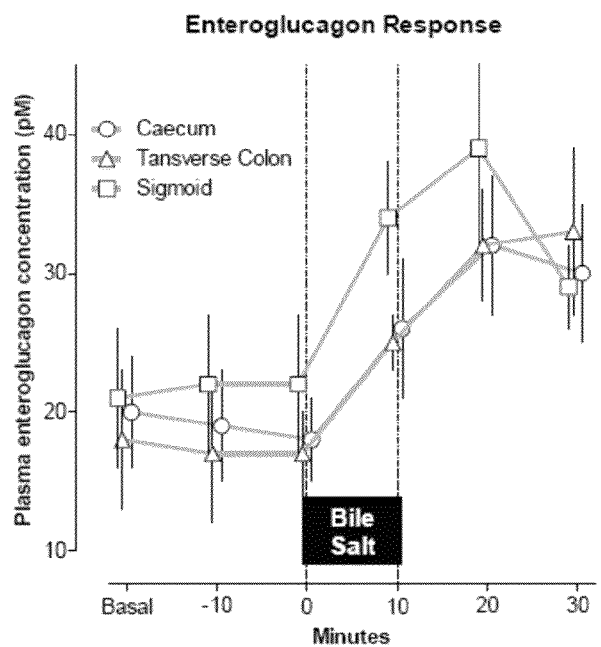
FIG. 1B illustrates the plasma enteroglucagon concentrations in the caecum, transverse colon, and sigmoid as a result of bile salt administration.

In certain embodiments, enteroendocrine peptide secretion enhancing agents used in the methods and compositions described herein enhance the secretion of an enteroendocrine peptide secreted by L-cells (e.g., GLP-1, GLP-2, PYY, and the like). FIG. 1 (FIGS. 1A and 1B) illustrates the response of enteroendocrine peptides to administration of bile salts.

In some embodiments, the enteroendocrine peptide secretion enhancing agent is a steroid acid, such as a bile acid/salt, a bile acid/salt mimic, a modified bile acid/salt, or a combination thereof. The bile acids or salts thereof used in the methods and compositions described herein include, by way of non-limiting example, cholic acid, deoxycholic acid, glycocholic acid, glycodeoxycholic acid, taurocholic acid, taurodihydrofusidate, taurodeoxycholic acid, cholate, glycocholate, deoxycholate, taurocholate, taurodeoxycholate, chenodeoxycholic acid, ursodeoxycholic acid and combinations thereof. In certain embodiments, bile salts used in the methods and compositions described herein are pharmaceutically acceptable salts including, by way of non-limiting example, the sodium and potassium salts thereof. In specific embodiments, the enteroendocrine peptide secretion enhancing agent is a pharmaceutically acceptable bile acid salt including, by way of non-limiting example, sodium glycocholate, sodium taurocholate and combinations thereof. In some embodiments, more than one bile acid and/or salt is used in a methods and/or composition described herein. In certain embodiments, the bile acid/salt used herein has a low or relatively low solubility in water.

Although bile acids facilitate digestion and absorption of lipids in the small intestine, they are generally used in pharmaceutical formulations as excipients. As excipients, bile acids find uses as surfactants and/or as agents that enhance the transfer of active components across mucosal membranes, for systemic delivery of a pharmaceutically active compound. In certain embodiments of the methods and pharmaceutical compositions described herein, however, a bile acid, a bile acid mimic and/or a modified bile acid is the active agent used to enhance secretion of enteroendocrine peptides.

In certain specific embodiments, the enteroendocrine peptide secretion enhancing agents used in the methods and compositions described herein are modified bile acids/salts. In certain embodiments, the bile acid/salt is modified in such a way so as to inhibit absorption of the bile acid/salt across the rectal or colonic mucosa.

In certain embodiments, the enteroendocrine peptide secretion enhancing agents described herein are a glucagon-like peptide secretion enhancing agent. In a specific embodiment, the glucagon-like peptide secretion enhancing agent is a bile acid, a bile acid mimic or a modified bile acid. In some embodiments, the glucagon-like peptide secretion enhancing agents are selected from, by way of non-limiting example, glucagon-like peptide-1 (GLP-1) secretion enhancing agents or glucagon-like peptide-2 (GLP-2) secretion enhancing agents. In some embodiments, the glucagon-like peptide secretion enhancing agents enhance both GLP-1 and GLP-2. In a specific embodiment, the GLP-1 and/or GLP-2 secretion enhancing agent is selected from bile acids, bile acid mimics or modified bile acids.

In certain embodiments, the enteroendocrine peptide secretion enhancing agent described herein is a pancreatic polypeptide-fold peptide secretion enhancing agent. In more specific embodiments, the pancreatic polypeptide-fold peptide secretion enhancing agent is selected from, by way of non-limiting example, peptide YY (PYY) secretion enhancing agents. In specific embodiments, the pancreatic polypeptide-fold peptide secretion enhancing agent or the PYY secretion enhancing agent is selected from a bile acid, a bile acid mimic, a modified bile acid or a fatty acid or salt thereof (e.g., a short chain fatty acid).

In some embodiments, the enteroendocrine peptide secretion enhancing agent is selected from, by way of non-limiting example, carbohydrates, glucose, fats, and proteins. In certain embodiments, the enteroendocrine peptide secretion enhancing agent is selected from fatty acids, including long chain fatty acids and short chain fatty acids. Short chain fatty acids and salts include, by way of non-limiting example, propionic acid, butyric acid, propionate, and butyrate.

In some embodiments, the enteroendocrine peptide secretion enhancing agent is selected from, by way of non-limiting example, carbohydrates, glucose, fat, protein, protein hydrolysate, amino acids, nutrients, intestinal peptides, peripheral hormones that participate in energy homeostasis, such as the adipocyte hormone leptin, bile acids/salts, insulin, gastrin-releasing peptide (GRP), gut peptides, gastric acid, CCK, insulin-like growth factor 1, bombesin, calcitonin-gene-related peptide and combinations thereof that enhance the secretion of enteroendocrine peptides.

In certain embodiments, the inhibitors of degradation of L-cell enteroendocrine peptide products include DPP-IV inhibitors, TGR5 modulators (e.g., TGR5 agonists), or combinations thereof. In certain instances, the administration of a DPP-IV inhibitor in combination with any of the compounds disclosed herein reduces or inhibits degradation of GLP-1 or GLP-2. In certain instances, administration of a TGR5 agonist in combination with any of the compounds disclosed herein enhances the secretion of enteroendocrine peptide products from L-cells. In some instances, the enteroendocrine peptide enhancing agent agonizes or partially agonizes bile acid receptors (e.g., TGR5 receptors or Farnesoid-X receptors) on in the gastrointestinal tract.

DPP-IV inhibitors include (2S)-1-{2-[(3-hydroxy-1-adamantyl)amino]acetyl}pyrrolidine-2-carbonitrile (vildagliptin), (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin). TGR5 modulators (e.g., agonists) include the compounds disclosed in, e.g, WO2008/091540, WO 2008067219 and US Appl. No. 2008/0221161, the TGR5 modulators (e.g., agonists) of which are hereby incorporated herein by reference.

Figure 2:
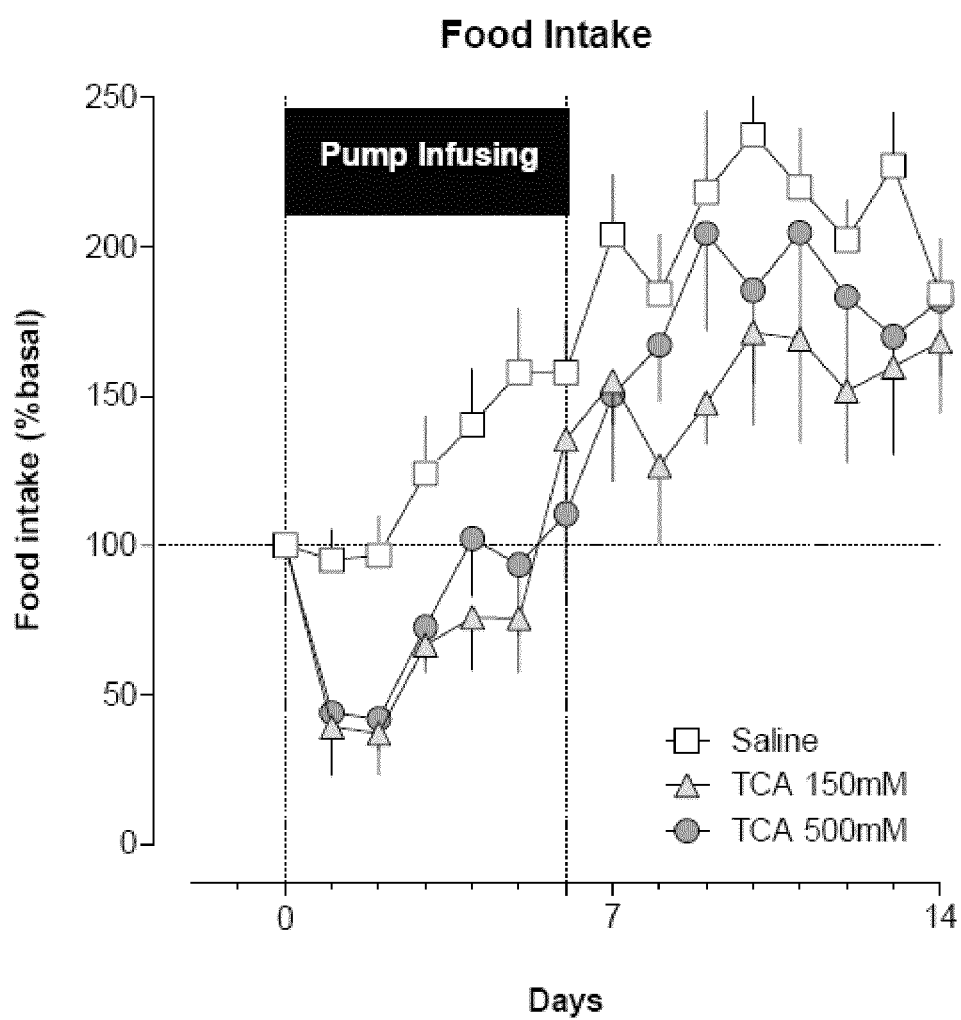
FIG. 2 illustrates the affect on food intake of pump infusion of TCA.
Figure 3:
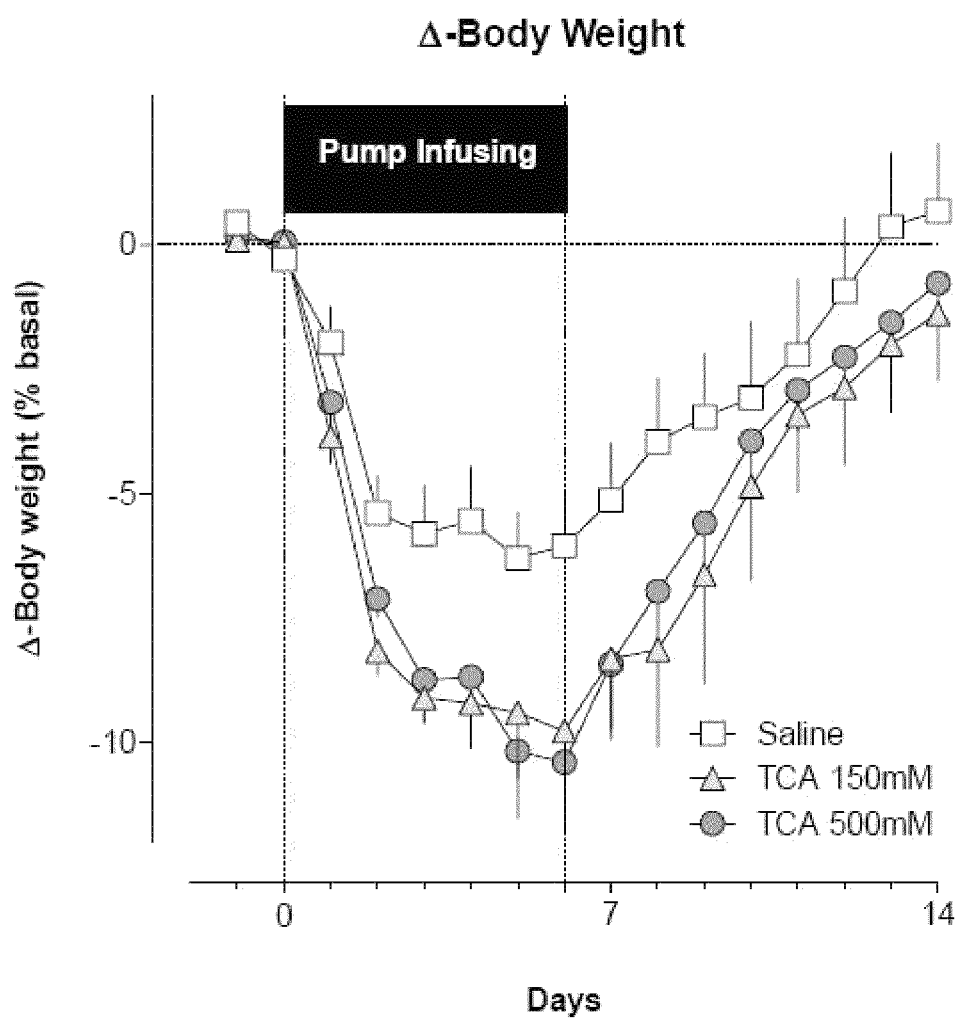
FIG. 3 illustrates the affect on body weight of pump infusion of TCA.

FIG. 2 illustrates the affect on food intake of pump infusion of TCA in concentrations of 150 mM and 500 mM. FIG. 3 illustrates the affect on body weight of pump infusion of TCA in concentrations of 150 mM and 500 mM.

Absorption Inhibitors

In certain embodiments, the compositions described herein are and the methods described herein include administering a composition that is formulated for the non-systemic delivery of enteroendocrine peptide secretion enhancing agents to the rectum and/or colon (sigmoid, transverse, and/or ascending colon). As previously discussed, enteroendocrine peptide secretion enhancing agents include, by way of non-limiting example, bile acids, bile salts, bile acid mimics, bile salt mimics, modified bile acids, modified bile salts and combinations thereof. In certain embodiments, the composition described herein as being formulated for the non-systemic delivery of enteroendocrine peptide secretion enhancing agents further includes an absorption inhibitor. As used herein, an absorption inhibitor includes an agent or group of agents that inhibit absorption of the enteroendocrine peptide secretion enhancing agent across the rectal or colonic mucosa. In specific embodiments, the absorption inhibitor is an absorption inhibitor that inhibits the absorption of the specific enteroendocrine peptide secretion enhancing agent with which it is combined.

Suitable bile acid absorption inhibitors (also described herein as absorption inhibiting agents) include, by way of non-limiting example, anionic exchange matrices, polyamines, quaternary amine containing polymers, quaternary ammonium salts, polyallylamine polymers and copolymers, colesevelam, colesevelam hydrochloride, CholestaGel (N,N,N-trimethyl-6-(2-propenylamino)-1-hexanaminium chloride polymer with (chloromethyl)oxirane, 2-propen-1-amine and N-2-propenyl-1-decanamine hydrochloride), cyclodextrins, chitosan, chitosan derivatives, carbohydrates which bind bile acids, lipids which bind bile acids, proteins and proteinaceous materials which bind bile acids, and antibodies and albumins which bind bile acids. Suitable cyclodextrins include those that bind bile acids such as, by way of non-limiting example, β-cyclodextrin and hydroxypropyl-β-cyclodextrin. Suitable proteins, include those that bind bile acids such as, by way of non-limiting example, bovine serum albumin, egg albumin, casein, $\alpha^1$-acid glycoprotein, gelatin, soy proteins, peanut proteins, almond proteins, and wheat vegetable proteins.

In certain embodiments the absorption inhibitor is cholestyramine. In specific embodiments, cholestyramine is combined with a bile acid. Cholestyramine, an ion exchange resin, is a styrene polymer containing quaternary ammonium groups crosslinked by divinylbenzene. In other embodiments, the absorption inhibitor is colestipol. In specific embodiments, colestipol is combined with a bile acid. Colestipol, an ion exchange resin, is a copolymer of diethylenetriamine and 1-chloro-2,3-epoxypropane.

In certain embodiments of the compositions and methods described herein the enteroendocrine peptide secretion enhancing agent is linked to an absorption inhibitor, while in other embodiments the enteroendocrine peptide secretion enhancing agent and the absorption inhibitor are separate molecular entities. In specific embodiments the bile acid, bile acid mimic or the modified bile acid is linked to a bile acid adsorption inhibitor described herein.

Cholesterol Absorption Inhibitors

In certain embodiments, a composition described herein optionally includes at least one cholesterol absorption inhibitor. Suitable cholesterol absorption inhibitors include, by way of non-limiting example, ezetimibe (SCH 58235), ezetimibe analogs, ACT inhibitors, stigmastanyl phosphorylcholine, stigmastanyl phosphorylcholine analogues, β-lactam cholesterol absorption inhibitors, sulfate polysaccharides, neomycin, plant sponins, plant sterols, phytostanol preparation FM-VP4, Sitostanol, β-sitosterol, acyl-CoA:cholesterol-O-acyltransferase (ACAT) inhibitors, Avasimibe, Implitapide, steroidal glycosides and the like. Suitable enzetimibe analogs include, by way of non-limiting example, SCH 48461, SCH 58053 and the like. Suitable ACT inhibitors include, by way of non-limiting example, trimethoxy fatty acid anilides such as Cl-976, 3-[decyldimethylsilyl]-N-[2-(4-methylphenyl)-1-phenylethyl]-propanamide, melinamide and the like. β-lactam cholesterol absorption inhibitors include, by way of non-limiting example, (3R-4S)-1,4-bis-(4-methoxyphenyl)-3-(3-phenylpropyl)-2-azetidinone and the like.

Enteroendocrine Peptides

In certain embodiments, the compositions described herein optionally include at least one enteroendocrine peptide. Suitable enteroendocrine peptides include, by way of non-limiting example, glucagon-like peptides GLP-1 and/or GLP-2, or pancreatic polypeptide-fold peptides pancreatic polypeptide (PP), neuropeptide Y (NPY) and/or peptide YY (PYY).

Peptidase Inhibitors

In some embodiments, the compositions described herein optionally include at least one peptidase inhibitor. Such peptidase inhibitors include, but are not limited to, dipeptidyl peptidase-4 inhibitors (DPP-4), neutral endopeptidase inhibitors, and converting enzyme inhibitors. Suitable dipeptidyl peptidase-4 inhibitors (DPP-4) include, by way of non-limiting example, Vildaglipti, 2S)-1-{2-[(3-hydroxy-1-adamantyl)amino]acetyl}pyrrolidine-2-carbonitrile, Sitagliptin, (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one, Saxagliptin, and (1S,3S,5S)-2-[(2S)-2-amino-2-(3-hydroxy-1-adamantyl)acetyl]-2-azabicyclo[3.1.0]hexane-3-carbonitrile. Such neutral endopeptidase inhibitors include, but are not limited to, Candoxatrilat and Ecadotril.

Spreading Agents/Wetting Agents

In certain embodiments, the composition described herein optionally comprises a spreading agent. In some embodiments, a spreading agent is utilized to improve spreading of the composition in the colon and/or rectum. Suitable spreading agents include, by way of non-limiting example, hydroxyethylcellulose, hydroxypropymethyl cellulose, polyethylene glycol, colloidal silicon dioxide, propylene glycol, cyclodextrins, microcrystalline cellulose, polyvinylpyrrolidone, polyoxyethylated glycerides, polycarbophil, di-n-octyl ethers, Cetiol™OE, fatty alcohol polyalkylene glycol ethers, Aethoxal™B), 2-ethylhexyl palmitate, Cegesoft™C 24), and isopropyl fatty acid esters.

In some embodiments, the compositions described herein optionally comprise a wetting agent. In some embodiments, a wetting agent is utilized to improve wettability of the composition in the colon and rectum. Suitable wetting agents include, by way of non-limiting example, surfactants. In some embodiments, surfactants are selected from, by way of non-limiting example, polysorbate (e.g., 20 or 80), stearyl hetanoate, caprylic/capric fatty acid esters of saturated fatty alcohols of chain length $C_{12}$-$C_{18}$, isostearyl diglycerol isostearic acid, sodium dodecyl sulphate, isopropyl myristate, isopropyl palmitate, and isopropyl myristate/isopropyl stearate/isopropyl palmitate mixture.

Methods

In certain embodiments, provided herein is a method of treating a metabolic disease or a condition associated with a metabolic disease with an enteroendocrine peptide secretion enhancing agent and an optional carrier. In some embodiments, provided herein are methods of treating a metabolic disease comprising administering any composition as described herein. In some embodiments, provided herein is the use of any of the pharmaceutical compositions described herein in preparing a medicament for treating a metabolic disease. In specific embodiments, the metabolic disease is selected from, by way of non-limiting example, obesity, diabetes, and a combination thereof. In some embodiments, provided herein is a method of treating a condition associated with a metabolic disease. In certain embodiments, provided herein is the use of any of the pharmaceutical compositions described herein in preparing a medicament for treating a condition associated with a metabolic disease. In some embodiments, conditions associated with a metabolic disease are selected from, by way of non-limiting example, weight gain, food intake, appetite, impaired glucose tolerance, a glucose metabolic disorder, and insulin resistance. In certain embodiments, conditions associated with a metabolic disease are selected from, by way of non-limiting example, acute coronary syndrome, hibernating myocardium, ventricular dysfunction, cardiac risk, post myocardial infarction mortality, post-surgical catabolism, sepsis-related catabolism, critical illness-related catabolism, post-surgical mortality, sepsis-related mortality, critical illness-related mortality, critical illness-polyneuropathy, congestive heart failure, toxic hypervolemia, renal failure, ischemia-reperfusion injury, mortality and morbitity from stroke, mortality and morbitity from neurodegenerative disease, neuropathy, inflammatory bowel disease, bowel mucosal injury, impaired bowel integrity, irritable bowel disease, osteopenia, and a bone fracture or a bone disorder. It is to be understood that the term, "treating" includes controlling, suppressing, inhibiting, reducing the symptoms of and/or preventing.

Furthermore, in certain embodiments, provided herein is a method of decreasing appetite, decreasing food intake, and/or decreasing appetite by administering a therapeutically effective amount of any enteroendocrine peptide secretion enhancing agent or composition described herein. In some embodiments, provided herein is an enteroendocrine peptide secretion enhancing agent or a composition used for preparing a medicament for decreasing appetite, decreasing food intake, and/or decreasing appetite.

In some embodiments, provided herein is a method of treating obesity or diabetes in an individual comprising delivering to ileal, colon, and/or rectal L-cells of the individual a therapeutically effective amount of any enteroendocrine peptide secretion enhancing agent described herein. In certain embodiments, the therapeutically effective amount of enteroendocrine peptide secretion enhancing agent stimulates or activates the L-cells to which the enteroendocrine peptide secretion enhancing agent is administered.

Figure 11:
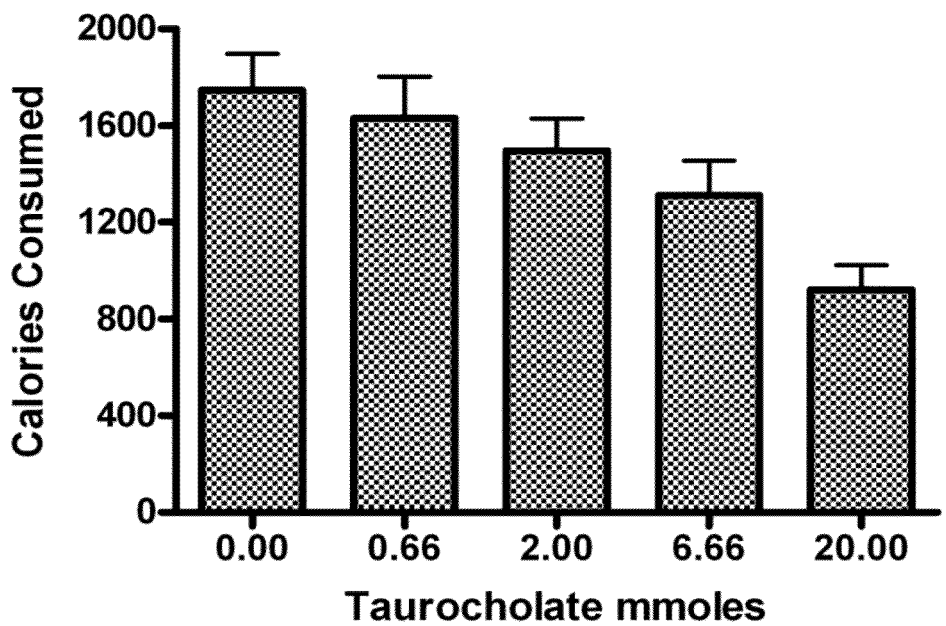
FIG. 11 illustrates the reduction of food intake in response to administration of bile acids in obese human diabetics.

FIG. 11 illustrates the reduction of food intake in response to administration of anenteroendocrine peptide secretion enhancing agent. FIG. 11 illustrates that with increased amounts of enteroendocrine peptide secretion enhancing agent administered to the distal gastrointestinal tract, decreased amounts of calories were consumed by human subjects.

In some embodiments, provided herein is a method of treating diabetes in an individual comprising delivering to ileal, colon, and/or rectal L-cells of an individual in need thereof a therapeutically effective amount of any enteroendocrine peptide secretion enhancing agent described herein. In certain embodiments, provided herein is a method of treating diabetes in an individual comprising delivering to ileum, colon, and/or rectum of an individual in need thereof a therapeutically effective amount of any enteroendocrine peptide secretion enhancing agent described herein. In some embodiments, provided herein is a method of elevating insulin levels in an individual comprising delivering to ileum, colon, and/or rectum of an individual in need thereof (e.g., a diabetic individual) a therapeutically effective amount of any enteroendocrine peptide secretion enhancing agent described herein. In certain embodiments, provided herein is a method of reducing glucose levels in an individual comprising delivering to ileum, colon, and/or rectum of an individual in need thereof (e.g., a diabetic individual) a therapeutically effective amount of any enteroendocrine peptide secretion enhancing agent described herein. In some embodiments, the therapeutically effective amount of enteroendocrine peptide secretion enhancing agent stimulates or activates the L-cells of the ileum, colon, and/or rectum to which the enteroendocrine peptide secretion enhancing agent is administered.

Figure 12:
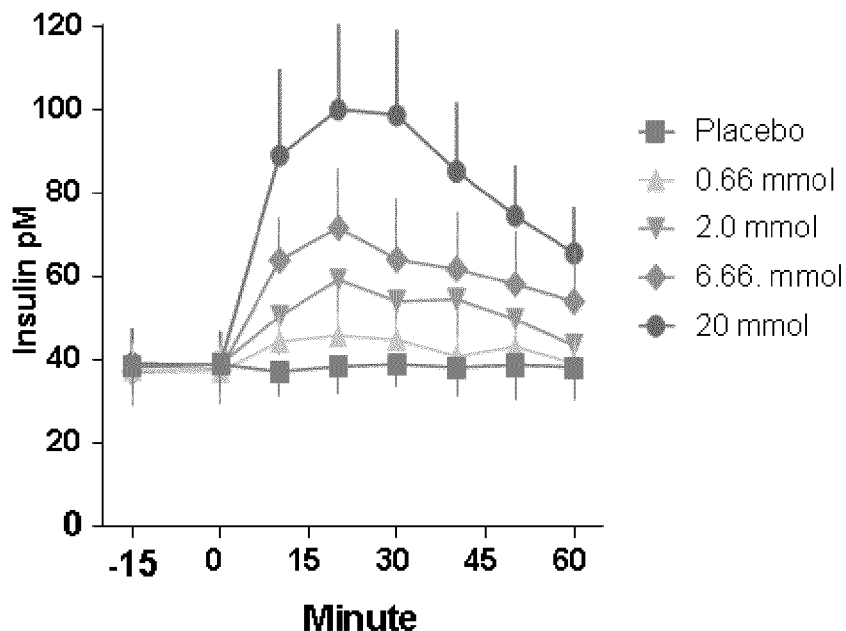
FIG. 12 illustrates the acute release of insulin and in response to administration of bile acids in obese human diabetics.
Figure 13:
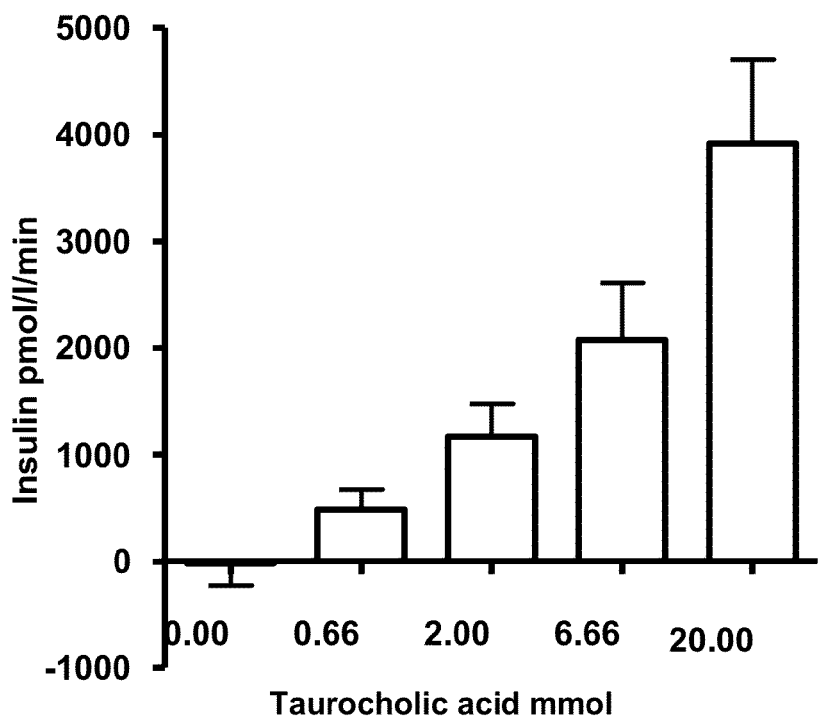
FIG. 13 illustrates the incremental integrated response of insulin to bile acids in obese human diabetics.

FIG. 12 illustrates the insulin response to administration of an enteroendocrine peptide secretion enhancing agent. FIG. 12 illustrates that with increased amounts of enteroendocrine peptide secretion enhancing agent administered to the distal gastrointestinal tract, human diabetics demonstrated increased levels of insulin. FIG. 13 illustrates the incremental integrated response of insulin levels to administration of an enteroendocrine peptide secretion enhancing agent.

Figure 14:
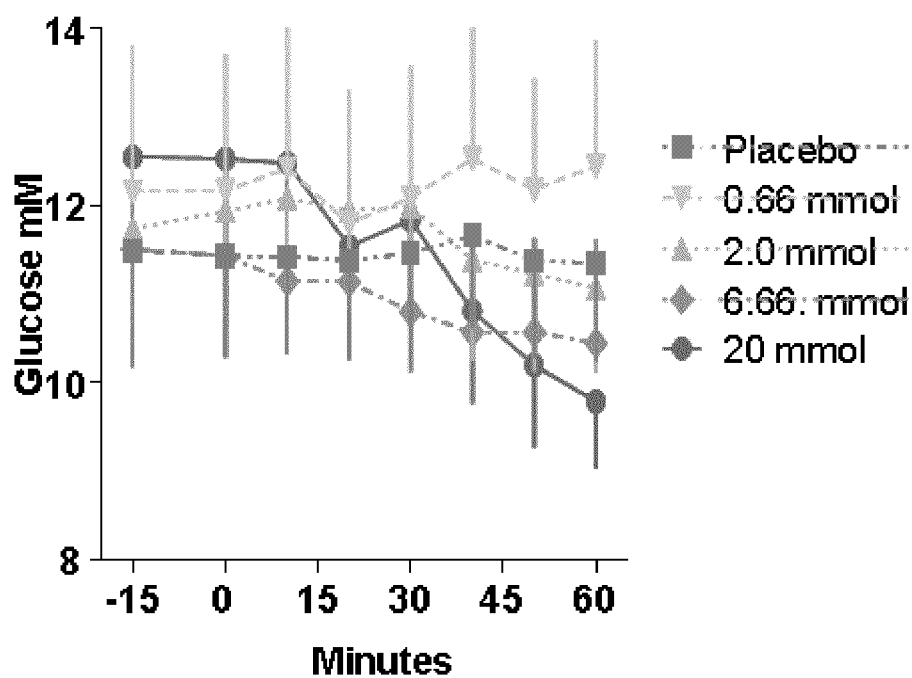
FIG. 14 illustrates the acute reduction of glucose in response to administration of bile acids in obese human diabetics.
Figure 15:
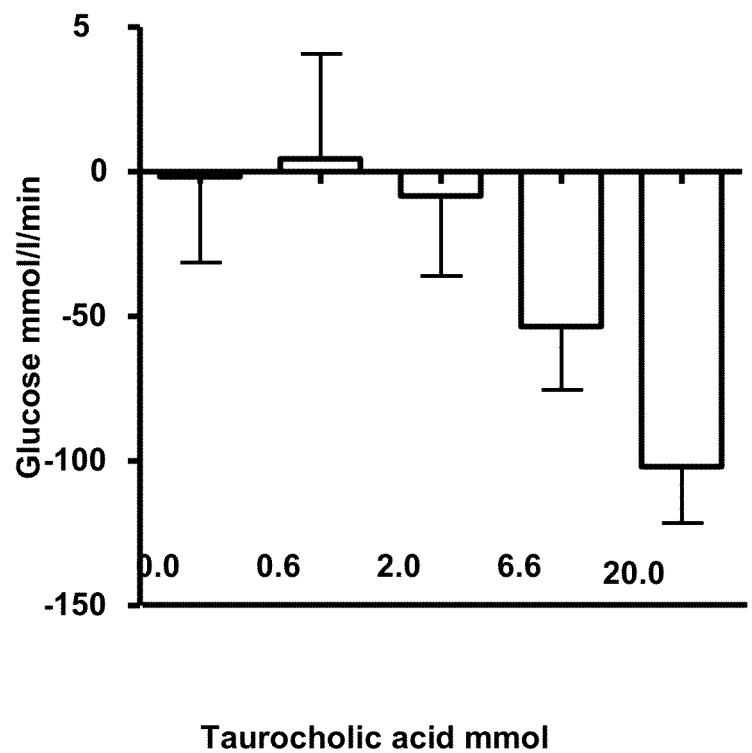
FIG. 15 illustrates the incremental integrated response of glucose to bile acids in obese human diabetics.

FIG. 14 illustrates the glucose response to administration of anenteroendocrine peptide secretion enhancing agent. FIG. 14 illustrates that with increased amounts of enteroendocrine peptide secretion enhancing agent administered to the distal gastrointestinal tract, human diabetics demonstrated decreased levels of glucose. FIG. 15 illustrates the incremental integrated response of glucose levels to administration of an enteroendocrine peptide secretion enhancing agent.

In some embodiments, provided herein is a method of elevating GLP-1, PYY, oxyntomodulin, insulin, or a combination thereof levels in an individual comprising delivering to ileum, colon, and/or rectum of an individual in need thereof (e.g., a diabetic individual) a therapeutically effective amount of any enteroendocrine peptide secretion enhancing agent described herein. In some embodiments, provided herein is a method of elevating GLP-1, PYY, oxyntomodulin, and insulin levels in an individual comprising delivering to ileum, colon, and/or rectum of an individual in need thereof (e.g., a diabetic individual) a therapeutically effective amount of any enteroendocrine peptide secretion enhancing agent described herein.

In certain embodiments, the pharmaceutical composition administered includes a therapeutically effective amount of an enteroendocrine peptide secretion enhancing agent, an absorption inhibitor and a carrier (e.g., an orally suitable carrier or a rectally suitable carrier, depending on the mode of intended administration). In certain embodiments, the pharmaceutical composition used or administered comprises an enteroendocrine peptide secretion enhancing agent, an absorption inhibitor, a carrier, and one or more of a cholesterol absorption inhibitor, an enteroendocrine peptide, a peptidase inhibitor, a spreading agent, and a wetting agent.

In a specific embodiment, the pharmaceutical composition used to prepare a rectal dosage form or administered rectally comprises an enteroendocrine peptide secretion enhancing agent, an absorption inhibitor, a rectally suitable carrier, an optional cholesterol absorption inhibitor, an optional enteroendocrine peptide, an optional peptidase inhibitor, an optional spreading agent, and an optional wetting agent. In certain embodiments, rectally administered compositions evokes an anorectal response. In specific embodiments, the anorectal response is an increase in secretion of one or more enteroendocrine by cells (e.g., L-cells) in the colon and/or rectum (e.g., in the epithelial layer of the colon and/or rectum). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

In another specific embodiment, the pharmaceutical composition used to prepare an oral dosage form or administered orally comprises an enteroendocrine peptide secretion enhancing agent, an absorption inhibitor, an orally suitable carrier, an optional cholesterol absorption inhibitor, an optional enteroendocrine peptide, an optional peptidase inhibitor, an optional spreading agent, and an optional wetting agent. In certain embodiments, the orally administered compositions evokes an anorectal response. In specific embodiments, the anorectal response is an increase in secretion of one or more enteroendocrine by cells in the colon and/or rectum (e.g., in L-cells the epithelial layer of the colon and/or rectum). In some embodiments, the anorectal response persists for at least 1, 2, 3, 4, 5, 6, 7, 8, 9, 10, 11, 12, 13, 14, 15, 16, 17, 18, 19, 20, 21, 22, 23 or 24 hours. In other embodiments the anorectal response persists for a period between 24 hours and 48 hours, while in other embodiments the anorectal response persists for persists for a period greater than 48 hours.

Provided herein are methods for prevention and/or treatment of congestive heart failure, ventricular dysfunction, toxic hypervolemia, polycystic ovary syndrome, inflammatory bowel disease, impaired bowel integrity, short bowel syndrome, gastritis, peptic ulcer, or irritable bowel disease comprising contacting the distal gastrointestinal tract (e.g., colon and/or rectum) of an individual in need thereof with an enteroendocrine peptide secretion enhancing agent and an optional absorption inhibitor. In some embodiments, the methods further comprise administration of a DPP-IV inhibitor, a TGR5 agonist, a biguanide, an incretin mimetic, or GLP-1 or an analog thereof. Provided herein are methods for prevention and/or treatment of radiation enteritis comprising contacting the distal gastrointestinal tract (e.g., colon and/or rectum) of an individual in need thereof with an enteroendocrine peptide secretion enhancing agent and an optional absorption inhibitor. In some embodiments, the methods further comprise administration of a DPP-IV inhibitor, a TGR5 agonist, a biguanide, an incretin mimetic, or GLP-1 or an analog thereof. Provided in certain embodiments herein is a method of promoting regeneration of the gastrointestinal tract by administering to the distal gastrointestinal tract (e.g., colon and/or rectum) of the individual, a therapeutically effective amount of an enteroendocrine peptide secretion enhancing agent and an optional absorption inhibitor. In some embodiments, the methods further comprise administration of a DPP-IV inhibitor, a TGR5 agonist, a biguanide, an incretin mimetic, or GLP-2 or an analog thereof. In some instances, radiation enteritis, or an inflammation of the intestine, is not only major complication of cancer radiation therapy, but occur after any accidental and intentional radiation exposure. In certain instances, GLP-2 secreted from L-cells (e.g., by administration thereto an enteroendocrine peptide secretion enhancing agent described herein) plays important role in regeneration of GI tract injuries.

Routes of Administration and Dosage

In some embodiments, the compositions described herein and the compositions administered in the methods described herein are formulated to enhance enteroendocrine peptide secretion and to evoke an anorectal response. In certain embodiments, the compositions described herein are formulated for rectal or oral administration. In some embodiments, such formulations are administered rectally or orally, respectively. In some embodiments, the compositions described herein are combined with a device for local delivery of the compositions to the rectum and/or colon (sigmoid colon, transverse colon, or ascending colon). In certain embodiments, for rectal administration the composition described herein are formulated as enemas, rectal gels, rectal foams, rectal aerosols, suppositories, jelly suppositories, or retention enemas. In some embodiments, for oral administration the compositions described herein are formulated for oral administration and enteric delivery to the colon.

In certain embodiments, the compositions or methods described herein are non-systemic. In some embodiments, compositions described herein deliver the enteroendocrine peptide secretion enhancing agent to the distal ileum, colon, and/or rectum and not systemically (e.g., a substantial portion of the enteroendocrine peptide secretion enhancing agent is not systemically absorbed). In some embodiments, oral compositions described herein deliver the enteroendocrine peptide secretion enhancing agent to the distal ileum, colon, and/or rectum and not systemically (e.g., a substantial portion of the enteroendocrine peptide secretion enhancing agent is not systemically absorbed). In some embodiments, rectal compositions described herein deliver the enteroendocrine peptide secretion enhancing agent to the distal ileum, colon, and/or rectum and not systemically (e.g., a substantial portion of the enteroendocrine peptide secretion enhancing agent is not systemically absorbed). In certain embodiments, non-systemic compositions described herein deliver less than 90% w/w of the enteroendocrine peptide secretion enhancing agent systemically. In certain embodiments, non-systemic compositions described herein deliver less than 80% w/w of the enteroendocrine peptide secretion enhancing agent systemically. In certain embodiments, non-systemic compositions described herein deliver less than 70% w/w of the enteroendocrine peptide secretion enhancing agent systemically. In certain embodiments, non-systemic compositions described herein deliver less than 60% w/w of the enteroendocrine peptide secretion enhancing agent systemically. In certain embodiments, non-systemic compositions described herein deliver less than 50% w/w of the enteroendocrine peptide secretion enhancing agent systemically. In certain embodiments, non-systemic compositions described herein deliver less than 40% w/w of the enteroendocrine peptide secretion enhancing agent systemically. In certain embodiments, non-systemic compositions described herein deliver less than 30% w/w of the enteroendocrine peptide secretion enhancing agent systemically. In certain embodiments, non-systemic compositions described herein deliver less than 25% w/w of the enteroendocrine peptide secretion enhancing agent systemically. In certain embodiments, non-systemic compositions described herein deliver less than 20% w/w of the enteroendocrine peptide secretion enhancing agent systemically. In certain embodiments, non-systemic compositions described herein deliver less than 15% w/w of the enteroendocrine peptide secretion enhancing agent systemically. In certain embodiments, non-systemic compositions described herein deliver less than 10% w/w of the enteroendocrine peptide secretion enhancing agent systemically. In certain embodiments, non-systemic compositions described herein deliver less than 5% w/w of the enteroendocrine peptide secretion enhancing agent systemically. In some embodiments, systemic absorption is determined in any suitable manner, including the total circulating amount, the amount cleared after administration, or the like.

In certain embodiments, the compositions and/or formulations described herein are administered at least once a day. In certain embodiments, the formulations containing the enteroendocrine peptide secretion enhancing agents are administered at least twice a day, while in other embodiments the formulations containing the enteroendocrine peptide secretion enhancing agents are administered at least three times a day. In certain embodiments, the formulations containing the enteroendocrine peptide secretion enhancing agents are administered up to five times a day. It is to be understood that in certain embodiments, the dosage regimen of composition containing the enteroendocrine peptide secretion enhancing agents described herein to is determined by considering various factors such as the patient's age, sex, and diet.

The concentration of the enteroendocrine peptide secretion enhancing agents administered in the formulations described herein ranges from about 1 mM to about 1 M. In certain embodiments the concentration of the enteroendocrine peptide secretion enhancing agents administered in the formulations described herein ranges from about 1 mM to about 750 mM. In certain embodiments the concentration of the enteroendocrine peptide secretion enhancing agents administered in the formulations described herein ranges from about 1 mM to about 500 mM. In certain embodiments the concentration of the enteroendocrine peptide secretion enhancing agents administered in the formulations described herein ranges from about 5 mM to about 500 mM. In certain embodiments the concentration of the enteroendocrine peptide secretion enhancing agents administered in the formulations described herein ranges from about 10 mM to about 500 mM. In certain embodiments the concentration of the enteroendocrine peptide secretion enhancing agents administered in the formulations described herein ranges from about 25 mM to about 500 mM. In certain embodiments the concentration of the enteroendocrine peptide secretion enhancing agents administered in the formulations described herein ranges from about 50 mM to about 500 mM. In certain embodiments the concentration of the enteroendocrine peptide secretion enhancing agents administered in the formulations described herein ranges from about 100 mM to about 500 mM. In certain embodiments the concentration of the enteroendocrine peptide secretion enhancing agents administered in the formulations described herein ranges from about 200 mM to about 500 mM.

In certain embodiments, any composition described herein comprises a therapeutically effective amount (e.g., to treat obesity and/or diabetes) of an enteroendocrine peptide secretion enhancing agent (e.g., bile acid). In some embodiments, compositions described herein comprise or methods described herein comprise administering about 0.01 mg to about 10 g of an enteroendocrine peptide secretion enhancing agent (e.g., bile acid). In certain embodiments, a composition described herein comprises or a method described herein comprises administering about 0.1 mg to about 500 mg of an enteroendocrine peptide secretion enhancing agent (e.g., bile acid). In certain embodiments, a composition described herein comprises or a method described herein comprises administering about 0.1 mg to about 100 mg of an enteroendocrine peptide secretion enhancing agent (e.g., bile acid). In certain embodiments, a composition described herein comprises or a method described herein comprises administering about 0.1 mg to about 50 mg of an enteroendocrine peptide secretion enhancing agent (e.g., bile acid). In certain embodiments, a composition described herein comprises or a method described herein comprises administering about 0.1 mg to about 10 mg of an enteroendocrine peptide secretion enhancing agent (e.g., bile acid). In certain embodiments, a composition described herein comprises or a method described herein comprises administering about 0.5 mg to about 10 mg of an enteroendocrine peptide secretion enhancing agent (e.g., bile acid). In some embodiments, compositions described herein comprise or methods described herein comprise administering about 0.1 mmol to about 1 mol of an enteroendocrine peptide secretion enhancing agent (e.g., bile acid). In certain embodiments, a composition described herein comprises or a method described herein comprises administering about 0.01 mmol to about 500 mmol of an enteroendocrine peptide secretion enhancing agent (e.g., bile acid). In certain embodiments, a composition described herein comprises or a method described herein comprises administering about 0.1 mmol to about 100 mmol of an enteroendocrine peptide secretion enhancing agent (e.g., bile acid). In certain embodiments, a composition described herein comprises or a method described herein comprises administering about 0.5 mmol to about 30 mmol of an enteroendocrine peptide secretion enhancing agent (e.g., bile acid). In certain embodiments, a composition described herein comprises or a method described herein comprises administering about 0.5 mmol to about 20 mmol of an enteroendocrine peptide secretion enhancing agent (e.g., bile acid). In certain embodiments, a composition described herein comprises or a method described herein comprises administering about 1 mmol to about 10 mmol of an enteroendocrine peptide secretion enhancing agent (e.g., bile acid). In certain embodiments, a composition described herein comprises or a method described herein comprises administering about 0.01 mmol to about 5 mmol of an enteroendocrine peptide secretion enhancing agent (e.g., bile acid). In certain embodiments, a composition described herein comprises or a method described herein comprises administering about 0.1 mmol to about 1 mmol of an enteroendocrine peptide secretion enhancing agent (e.g., bile acid). In various embodiments, certain enteroendocrine peptide secretion enhancing agents (e.g., bile acids) have different potencies and dosing is optionally adjusted accordingly. For example, the investigation in TGR5-transfected CHO cells of TGR5 agonist potency of natural bile acids indicates the following rank of potency: Lithocholic acid (LCA) >deoxycholic acid (DCA)>murocholic acid (Muro-CA)>lagodeoxycholic acid (lago-DCA)>chenodeoxycholic (CDCA)>cholic acid (CA)>hyodeoxycholic acid (HDCA>ursodeoxycholic acid (UDCA); and assays on TGR5-transfected CHO cells demonstrate that $EC_{50}$ (in μM) for UDCA was 36.4, TauroCA (TCA) 4.95 and LCA 0.58.

In certain embodiments, by targeting the distal gastrointestinal tract (e.g., distal ileum, colon, and/or rectum), compositions and methods described herein provide efficacy (e.g., in reducing food intake, treating obesity, treating diabetes) with a reduced dose of enteroendocrine peptide secretion enhancing agent (e.g., as compared to an oral dose that does not target the distal gastrointestinal tract).

Rectal Administration Formulations

The pharmaceutical compositions described herein for the non-systemic delivery of enteroendocrine peptide secretion enhancing agents to the rectum and/or colon are formulated for rectal administration as rectal enemas, rectal foams, rectal gels, and rectal suppositories. The components of such formulations are described herein. It is to be understood that as used herein, pharmaceutical compositions and compositions are or comprise the formulations as described herein.

Rectal Enemas

In certain embodiments, the compositions described herein are formulated as rectal enema formulations for non-systemic delivery of enteroendocrine peptide secretion enhancing agents. In certain embodiments, such rectal enemas are formulated as a solution, aqueous suspension or emulsion. In some embodiments, solution enemas contain a carrier vehicle, an enteroendocrine peptide secretion enhancing agent, an absorption inhibitor (e.g., of the enteroendocrine peptide secretion enhancing agent across the rectal or colonic mucosa), and one or more of the following: a solubilizer, a preservative, a chelating agent, a buffer for pH regulation, and a thickener. In certain embodiments, rectal enemas are formulated as an emulsion or aqueous suspension containing a carrier vehicle, at least one enteroendocrine peptide secretion enhancing agent, at least one agent for inhibiting absorption of the enteroendocrine peptide secretion enhancing agent across the rectal or colonic mucosa, and one or more of the following: a preservative, a chelating agent, a buffer for pH regulation, a solubilizer, a thickener, and an emulsifier/surfactant.

In certain embodiments, rectal enemas are formulated such that a enteroendocrine peptide secretion enhancing agent is dissolved or dispersed in a suitable flowable carrier vehicle, including but not limited to water, alcohol or an aqueous-alcoholic mixture. In certain embodiments, the carrier vehicle is thickened with natural or synthetic thickeners. In further embodiments the rectal enema formulations also contain a lubricant.

In some embodiments, unit dosages of such enema formulations are administered from prefilled bags or syringes.

In certain embodiments, the volume of enema administered using such rectal enema formulations is a volume suitable for achieving a desired result, e.g., from about 10 mL to about 1000 mL. In certain embodiments, the volume of enema administered using such rectal enema formulations is from about 10 mL to about 900 mL. In certain embodiments, the volume of enema administered using such rectal enema formulations is from about 10 mL to about 800 mL. In certain embodiments, the volume of enema administered using such rectal enema formulations is from about 10 mL to about 700 mL. In certain embodiments, the volume of enema administered using such rectal enema formulations is from about 10 mL to about 600 mL. In certain embodiments, the volume of enema administered using such rectal enema formulations is from about 10 mL to about 500 mL. In certain embodiments, the volume of enema administered using such rectal enema formulations is from about 10 mL to about 400 mL. In certain embodiments, the volume of enema administered using such rectal enema formulations is from about 10 mL to about 300 mL. In certain embodiments, the volume of enema administered using such rectal enema formulations is from about 10 mL to about 200 mL. In certain embodiments, the volume of enema administered using such rectal enema formulations is from about 10 mL to about 100 mL.

Rectal Foams

In certain instances, leakage is a problem associated with enemas. As such, it is often desirable or necessary for patients to lie down during administration of enemas. In some embodiments, rectal administration using foams overcomes the problem of leakage from the rectum following administration.

In certain embodiments, the pharmaceutical compositions are formulated as rectal foams. In some embodiments, rectal foams are used for the rectal administration and for local or non-systemic delivery of enteroendocrine peptide secretion enhancing agents to the rectum and/or colon. Such rectal foams formulations contain an enteroendocrine peptide secretion enhancing agent dissolved or suspended in a liquid carrier vehicle, an absorption inhibitor (e.g., of the enteroendocrine peptide secretion enhancing agent across the rectal or colonic mucosa), a surfactant/emulsifier with foaming properties and a propellant (e.g., a propellant gas). In certain embodiments, rectal foam formulations also contain one or more of the following: a suspending/solubilizing agent, a thickener, a preservative, a chelating agent, a buffer, an antioxidant, a tonicity modifiers, and a spreading agent. In certain embodiments, surfactants/emulsifiers include, by way of non-limiting example, non-ionic surfactants, anionic surfactants, cationic surfactants, and combinations thereof.

In certain embodiments, rectal foam formulations are filled in pressurized containers prior to rectal administration. In certain embodiments the pressurized container is a can. In certain embodiments, propellants used herein include, by way of non-limiting example, hydrocarbons (such as isobutane, N-butane or propane), fluorocarbons (e.g. dichlorodifluoromethane and dichlorotetrafluoroethane), chlorofluorocarbons, dimethyl ether, hydrofluorocarbons, compressed gases, freon (such as freon 12, freon 114), hydrochlorofluorocarbons, hydrofluorocarbons or mixtures thereof.

In some embodiments, the maximum amount of propellant used is determined by its miscibility with other components in the composition to form a mixture, such as a homogeneous mixture. In certain embodiments, the minimal level of propellant used in the composition is determined by the desired foam characteristics, and its ability to substantially or completely evacuate the container.

In some embodiments, the propellant concentration used in such rectal foam formulations is about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 50%, 55% to about 60% (w/w).

In certain embodiments, rectal foams are formed upon rectal administration, wherein the dispensing valve of the can allows rapid expansion of the propellant, triggering the foaming action of the surfactant and resulting foam forms within the rectum and colon. In other embodiments, the rectal foams used for rectal administration of the compositions described herein are formed within the dispensing container prior to rectal administration.

The distance the foam can reach within the colon and rectum is controlled by controlling the foam propelling properties by varying the type and quantity of propellant used. The volume of foam administered using such rectal foam formulations is from about 10 mL to about 1000 mL. In certain embodiments, the volume of a composition described herein (e.g., a foam) described herein or used in a method described herein (e.g., a foam, enema, or gel) is from about 10 mL to about 900 mL. In certain embodiments, the volume of a composition described herein (e.g., a foam) described herein or used in a method described herein (e.g., a foam, enema, or gel) is from about 10 mL to about 800 mL. In certain embodiments, the volume of a composition described herein (e.g., a foam) described herein or used in a method described herein (e.g., a foam, enema, or gel) is from about 10 mL to about 700 mL. In certain embodiments, the volume of a composition described herein (e.g., a foam) described herein or used in a method described herein (e.g., a foam, enema, or gel) is from about 10 mL to about 600 mL. In certain embodiments, the volume of a composition described herein (e.g., a foam) described herein or used in a method described herein (e.g., a foam, enema, or gel) is from about 10 mL to about 500 mL. In certain embodiments, the volume of a composition described herein (e.g., a foam) described herein or used in a method described herein (e.g., a foam, enema, or gel) is from about 10 mL to about 400 mL. In certain embodiments, the volume of a composition described herein (e.g., a foam) described herein or used in a method described herein (e.g., a foam, enema, or gel) is from about 10 mL to about 300 mL. In certain embodiments, the volume of a composition described herein (e.g., a foam) described herein or used in a method described herein (e.g., a foam, enema, or gel) is from about 10 mL to about 200 mL. In certain embodiments, the volume of a composition described herein (e.g., a foam) described herein or used in a method described herein (e.g., a foam, enema, or gel) is from about 10 mL to about 100 mL. In specific embodiments, the volume of a composition described herein (e.g., a foam) described herein or used in a method described herein (e.g., a foam, enema, or gel) is about 20 mL to about 60 mL, about 20 mL, about 40 mL, or about 60 mL.

Rectal Gels

In some embodiments, the pharmaceutical compositions described herein are formulated as rectal gels. In certain embodiments, the rectal gels are suitable for the regional or local non-systemic administration of one or more enteroendocrine peptide secretion enhancing agents to the rectum and/or colon. In some embodiments, rectal gel formulations contain at least one enteroendocrine peptide secretion enhancing agent dissolved or suspended in a solvent/liquid carrier vehicle, an absorption inhibitor (e.g., of the enteroendocrine peptide secretion enhancing agent across the rectal or colonic mucosa) and at least one thickening agents. In certain embodiments such rectal gel formulations also contain one or more of the following: a buffering agent(s), a preservative(s), and an antioxidant(s).

In certain embodiments, rectal gels have gel-like consistencies but are sufficiently flowable so as to be capable of local or regional administration through a catheter, needle, syringe, or other comparable means of local or regional administration.

In some embodiments, the concentration of a thickener used in a rectal gel formulation is in an amount or concentration suitable to achieve a desired thickness or viscosity, e.g., from about 0.05% to about 10% by weight. In certain embodiments, the concentration of the thickener used in such rectal gel formulations ranges from about 0.05% to about 8% by weight. In certain embodiments, the concentration of the thickener used in such rectal gel formulations ranges from about 0.05% to about 7% by weight. In certain embodiments, the concentration of the thickener used in such rectal gel formulations ranges from about 0.05% to about 6% by weight. In certain embodiments, the concentration of the thickener used in such rectal gel formulations ranges from about 0.05% to about 5% by weight. In certain embodiments, the concentration of the thickener used in such rectal gel formulations ranges from about 0.05% to about 4% by weight. In certain embodiments, the concentration of the thickener used in such rectal gel formulations ranges from about 0.05% to about 3% by weight. In certain embodiments, the concentration of the thickener used in such rectal gel formulations ranges from about 0.05% to about 2% by weight. In certain embodiments, the concentration of the thickener used in such rectal gel formulations ranges from about 0.05% to about 1% by weight. In certain embodiments the rectal gel formulation includes methyl cellulose having a concentration from about 0.05% to about 2%, while in other embodiments the rectal gel formulation includes methyl cellulose having a concentration of about 1%.

Figure 4:
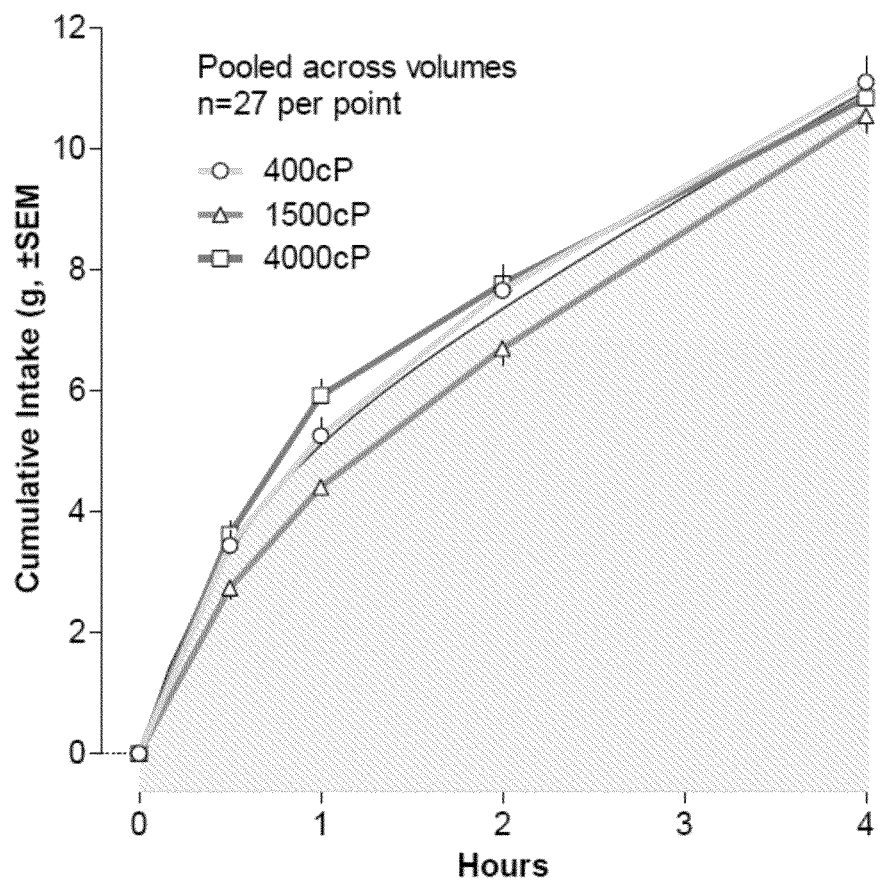
FIG. 4 illustrates the affect of the viscosity of a formulation described herein on the food intake of a subject.

In some embodiments, the any formulation described herein (e.g., arectal gel formulation) has a viscosity ranging from about 500 to about 50,000 centipoise (cP) at 25 C. In certain embodiments, the viscosity of the formulation described herein is from about 500 to about 40,000 centipoise (cP) at 25 C. In certain embodiments, the viscosity of the formulation described herein is from about 500 to about 30,000 centipoise (cP) at 25 C. In certain embodiments, the viscosity of the formulation described herein is from about 500 to about 20,000 centipoise (cP) at 25 C. In certain embodiments, the viscosity of the formulation described herein is from about 500 to about 10,000 centipoise (cP) at 25 C. In some embodiments, the formulation has a final viscosity of less than about 40,000 centipoises (cP), 20,000 cP, 15,000 cP, or 10,000 cP at 25 C. In some embodiments, the formulation has a viscosity of about 5,000 cP, 6,000 cP, 7,000 cP, 8,000 cP, 9,000 cP, 10,000 cP, 12,000 cP, 15,000 cP, 18,000 cP, 20,000 cP, 25,000 cP, 30,000 cP, 35,000 cP, or 40,000 cP at 25 C. In some embodiments, the formulation has a viscosity of about 1,000-20,000 cP, 5,000-15,000 cP, 6,000-12,000 cP, 7,000-10,000, 500-3500 cP, 500-300 cP, 1,000-2,000 cP, or about 1,500 cP at 25 C. In specific embodiments, the formulation has a viscosity of 1,000 cP to about 2,500 cP, or about 1,500 cP at 25 C. In certain embodiments, the amount of thickener used in a composition described herein is sufficient to achieve a viscosity as described herein. FIG. 4 illustrates the affect of the viscosity of a formulation described herein on the food intake of a subject.

In some embodiments, unit dosages of such rectal gel formulations are administered from prefilled bags or syringes.

Rectal Suppositories

In some embodiments, the pharmaceutical compositions described herein are also formulated as a suppository. In certain embodiments, suppositories are formulated for the regional or local non-systemic administration of one or more enteroendocrine peptide secretion enhancing agents to the rectum and/or colon.

In some embodiments, rectal suppository formulations contain a enteroendocrine peptide secretion enhancing agent, an absorption inhibitor (e.g., of the enteroendocrine peptide secretion enhancing agent across the rectal or colonic mucosa) and at least one pharmaceutically acceptable suppository base. In some embodiments, suppository formulation are prepared by combining an enteroendocrine peptide secretion enhancing agent with a pharmaceutically acceptable suppository base, melted, poured into a mould or moulds and cooled.

In certain embodiments, pharmaceutically acceptable suppository bases include, by way of non-limiting example, cocoa butter, beeswax, esterified fatty acids, glycerinated gelatin, semisynthetic glycerides of vegetable saturated fatty acids, polyethylene glycols, Witepsol, and polyoxyethylene sorbitan fatty acid esters.

In certain embodiments, the suppository formulations used to deliver one or more enteroendocrine peptide secretion enhancing agents to the rectum and/or colon also contain one or more of the following: buffering agents, preservatives, antioxidants, surfactants, and thickeners.

In some embodiments, suppositories contain from 0.5 to 10 mg of an enteroendocrine peptide secretion enhancing agent. In specific embodiments, suppositories contain from 1 to 5 mg of an enteroendocrine peptide secretion enhancing agent.

Components Used in Rectal Delivery/Administration Formulations

In certain embodiments, liquid carrier vehicles in the compositions and/or formulations described herein include, by way of non-limiting example, purified water, propylene glycol, polyethyleneglycol, ethanol, 1-propanol, 2-propanol, 1-propen-3-ol (allyl alcohol), propylene glycol, glycerol, 2-methyl-2-propanol, formamide, methyl formamide, dimethyl formamide, ethyl formamide, diethyl formamide, acetamide, methyl acetamide, dimethyl acetamide, ethyl acetamide, diethyl acetamide, 2-pyrrolidone, N-methyl-2-pyrrolidone, N-ethyl-2-pyrrolidone, tetramethyl urea, 1,3-dimethyl-2-imidazolidinone, propylene carbonate, 1,2-butylene carbonate, 2,3-butylene carbonate, dimethyl sulfoxide, diethyl sulfoxide, hexamethyl phosphoramide, pyruvic aldehyde dimethylacetal, dimethylisosorbide and combinations thereof.

In some embodiments, stabilizers used in compositions and/or formulations described herein include, but are not limited to, partial glycerides of polyoxyethylenic saturated fatty acids.

In certain embodiments, surfactants/emulsifiers used in the compositions and/or formulations described herein include, by way of non-limiting example, mixtures of cetostearylic alcohol with sorbitan esterified with polyoxyethylenic fatty acids, polyoxyethylene fatty ethers, polyoxyethylene fatty esters, fatty acids, sulfated fatty acids, phosphated fatty acids, sulfosuccinates, amphoteric surfactants, non-ionic poloxamers, non-ionic meroxapols, petroleum derivatives, aliphatic amines, polysiloxane derivatives, sorbitan fatty acid esters, laureth-4, PEG-2 dilaurate, stearic acid, sodium lauryl sulfate, dioctyl sodium sulfosuccinate, cocoamphopropionate, poloxamer 188, meroxapol 258, triethanolamine, dimethicone, polysorbate 60, sorbitan monostearate, pharmaceutically acceptable salts thereof, and combinations thereof.

In some embodiments, non-ionic surfactants used in compositions and/or formulations described herein include, by way of non-limiting example, phospholipids, alkyl poly(ethylene oxide), poloxamers, polysorbates, sodium dioctyl sulfosuccinate, Brij™-30 (Laureth-4), Brij™-58 (Ceteth-20) and Brij™-78 (Steareth-20), Brij™-721 (Steareth-21), Crillet-1 (Polysorbate 20), Crillet-2 (Polysorbate 40), Crillet-3 (Polysorbate 60), Crillet 45 (Polysorbate 80), Myrj-52 (PEG-40 Stearate), Myrj-53 (PEG-50 Stearate), Pluronic™ F77 (Poloxamer 217), Pluronic™ F87 (Poloxamer 237), Pluronic™ F98 (Poloxamer 288), Pluronic™ L62 (Poloxamer 182), Pluronic™ L64 (Poloxamer 184), Pluronic™ F68 (Poloxamer 188), Pluronic™ L81 (Poloxamer 231), Pluronic™ L92 (Poloxamer 282), Pluronic™ L101 (Poloxamer 331), Pluronic™ P103 (Poloxamer 333), Pluracare™ F 108 NF (Poloxamer 338), and Pluracare™ F 127 NF (Poloxamer 407) and combinations thereof. Pluronic™ polymers are commercially purchasable from BASF, USA and Germany.

In certain embodiments, anionic surfactants used in compositions and/or formulations described herein include, by way of non-limiting example, sodium laurylsulphate, sodium dodecyl sulfate (SDS), ammonium lauryl sulfate, alkyl sulfate salts, alkyl benzene sulfonate, and combinations thereof.

In some embodiments, the cationic surfactants used in compositions and/or formulations described herein include, by way of non-limiting example, benzalkonium chloride, benzethonium chloride, cetyl trimethylammonium bromide, hexadecyl trimethyl ammonium bromide, other alkyltrimethylammonium salts, cetylpyridinium chloride, polyethoxylated tallow and combinations thereof.

In certain embodiments, the thickeners used i in compositions and/or formulations described herein include, by way of non-limiting example, natural polysaccharides, semi-synthetic polymers, synthetic polymers, and combinations thereof. Natural polysaccharides include, by way of non-limiting example, acacia, agar, alginates, carrageenan, guar, arabic, tragacanth gum, pectins, dextran, gellan and xanthan gums. Semi-synthetic polymers include, by way of non-limiting example, cellulose esters, modified starches, modified celluloses, carboxymethylcellulose, methyl cellulose, ethyl cellulose, hydroxyethyl cellulose, hydroxypropyl cellulose and hydroxypropyl methylcellulose. Synthetic polymers include, by way of non-limiting example, polyoxyalkylenes, polyvinyl alcohol, polyacrylamide, polyacrylates, carboxypolymethylene (carbomer), polyvinylpyrrolidone (povidones), polyvinylacetate, polyethylene glycols and poloxamer. Other thickeners include, by way of nonlimiting example, polyoxyethyleneglycol isostearate, cetyl alcohol, Polyglycol 300 isostearate, propyleneglycol, collagen, gelatin, and fatty acids (e.g., lauric acid, myristic acid, palmitic acid, stearic acid, palmitoleic acid, linoleic acid, linolenic acid, oleic acid and the like).

In some embodiments, chelating agents used in the compositions and/or formulations described herein include, by way of non-limiting example, ethylenediaminetetraacetic acid (EDTA) or salts thereof, phosphates and combinations thereof.

In some embodiments, the concentration of the chelating agent or agents used in the rectal formulations described herein is a suitable concentration, e.g., about 0.1%, 0.15%, 0.2%, 0.25%, 0.3%, 0.4%, or 0.5% (w/v).

In some embodiments, preservatives used in compositions and/or formulations described herein include, by way of non-limiting example, parabens, ascorbyl palmitate, benzoic acid, butylated hydroxyanisole, butylated hydroxytoluene, chlorobutanol, ethylenediamine, ethylparaben, methylparaben, butyl paraben, propylparaben, monothioglycerol, phenol, phenylethyl alcohol, propylparaben, sodium benzoate, sodium propionate, sodium formaldehyde sulfoxylate, sodium metabisulfite, sorbic acid, sulfur dioxide, maleic acid, propyl gallate, benzalkonium chloride, benzethonium chloride, benzyl alcohol, chlorhexidine acetate, chlorhexidine gluconate, sorbic acid, potassium sorbitol, chlorbutanol, phenoxyethanol, cetylpyridinium chloride, phenylmercuric nitrate, thimerosol, and combnations thereof.

In certain embodiments, antioxidants used in compositions and/or formulations described herein include, by way of non-limiting example, ascorbic acid, ascorbyl palmitate, butylated hydroxyanisole, butylated hydroxytoluene, hypophosphorous acid, monothioglycerol, propyl gallate, sodium ascorbate, sodium sulfite, sodium bisulfite, sodium formaldehyde sulfoxylate, potassium metabisulphite, sodium metabisulfite, oxygen, quinones, t-butyl hydroquinone, erythorbic acid, olive (olea eurpaea) oil, pentasodium penetetate, pentetic acid, tocopheryl, tocopheryl acetate and combinations thereof.

In some embodiments, concentration of the antioxidant or antioxidants used in the rectal formulations described herein is sufficient to achieve a desired result, e.g., about 0.1%, 0.15%, 0.2%, 0.25%, 0.3%, 0.4%, or 0.5% (w/v).

The lubricating agents used in compositions and/or formulations described herein include, by way of non-limiting example, natural or synthetic fat or oil (e.g., a tris-fatty acid glycerate and the like). In some embodiments, lubricating agents include, by way of non-limiting example, glycerin (also called glycerine, glycerol, 1,2,3-propanetriol, and trihydroxypropane), polyethylene glycols (PEGs), polypropylene glycol, polyisobutene, polyethylene oxide, behenic acid, behenyl alcohol, sorbitol, mannitol, lactose, polydimethylsiloxane and combinations thereof.

In certain embodiments, mucoadhesive and/or bioadhesive polymers are used in the compositions and/or formulations described herein as agents for inhibiting absorption of the enteroendocrine peptide secretion enhancing agent across the rectal or colonic mucosa. Bioadhesive or mucoadhesive polymers include, by way of non-limiting example, hydroxypropyl cellulose, polyethylene oxide homopolymers, polyvinyl ether-maleic acid copolymers, methyl cellulose, ethyl cellulose, propyl cellulose, hydroxyethyl cellulose, hydroxypropyl cellulose, hydroxypropylmethyl cellulose, carboxymethylcellulose, polycarbophil, polyvinylpyrrolidone, carbopol, polyurethanes, polyethylene oxide-polypropyline oxide copolymers, sodium carboxymethyl cellulose, polyethylene, polypropylene, lectins, xanthan gum, alginates, sodium alginate, polyacrylic acid, chitosan, hyaluronic acid and ester derivatives thereof, vinyl acetate homopolymer, calcium polycarbophil, gelatin, natural gums, karaya, tragacanth, algin, chitosan, starches, pectins, and combinations thereof.

In some embodiments, buffers/pH adjusting agents used in compositions and/or formulations described herein include, by way of non-limiting example, phosphoric acid, monobasic sodium or potassium phosphate, triethanolamine (TRIS), BICINE, HEPES, Trizma, glycine, histidine, arginine, lysine, asparagine, aspartic acid, glutamine, glutamic acid, carbonate, bicarbonate, potassium metaphosphate, potassium phosphate, monobasic sodium acetate, acetic acid, acetate, citric acid, sodium citrate anhydrous, sodium citrate dihydrate and combinations thereof. In certain embodiments, an acid or a base is added to adjust the pH. Suitable acids or bases include, by way of non-limiting example, HCL, NaOH and KOH.

In certain embodiments, concentration of the buffering agent or agents used in the rectal formulations described herein is sufficient to achieve or maintain a physiologically desirable pH, e.g., about 0.1%, 0.2%, 0.3%, 0.4%, 0.5%, 0.6%, 0.8%, 0.9%, or 1.0% (w/w).

The tonicity modifiers used in compositions and/or formulations described herein include, by way of non-limiting example o, sodium chloride, potassium chloride, sodium phosphate, mannitol, sorbitol or glucose.

Devices

In certain aspects of the methods and pharmaceutical compositions described herein, a device is used for rectal administration of the compositions and/or formulations described herein (e.g., the rectal gels, rectal foams, enemas and suppositories described herein). In certain embodiments, rectal gels or rectal enemas are administered using a bag or a syringe, while rectal foams are administered using a pressurized container.

In certain embodiments, a perfusion system is used to rectally administer the pharmaceutical compositions and/or formulations described herein. In some embodiments, the system comprises a tube surrounded by a semi-permeable membrane is rectally inserted and a solution containing a composition described herein is pumped into the membrane. In certain embodiments, the membrane expands to contact the rectal and/or colon walls, wherein the enterendocrine peptide secretion enhancing agents perfuse from the inside of the membrane to the outside. In certain embodiments, the solution is re-circulated as a continuous perfusion system.

Oral Administration for Colonic Delivery

In certain aspects, the composition or formulation containing one or more enteroendocrine peptide secretion enhancing agents is orally administered for local delivery of an enteroendocrine peptide secretion enhancing agents to the colon and/or rectum. Unit dosage forms of such compositions include a pill, tablet or capsules formulated for enteric delivery to colon. In certain embodiments, such pills, tablets or capsule contain the compositions described herein entrapped or embedded in microspheres. In some embodiments, microspheres include, by way of non-limiting example, chitosan microcores HPMC capsules and cellulose acetate butyrate (CAB) microspheres. In certain embodiments, oral dosage forms are prepared using conventional methods known to those in the field of pharmaceutical formulation. For example, in certain embodiments, tablets are manufactured using standard tablet processing procedures and equipment. An exemplary method for forming tablets is by direct compression of a powdered, crystalline or granular composition containing the active agent(s), alone or in combination with one or more carriers, additives, or the like. In alternative embodiments, tablets are prepared using wet-granulation or dry-granulation processes. In some embodiments, tablets are molded rather than compressed, starting with a moist or otherwise tractable material.

In certain embodiments, tablets prepared for oral administration contain various excipients, including, by way of non-limiting example, binders, diluents, lubricants, disintegrants, fillers, stabilizers, surfactants, preservatives, coloring agents, flavoring agents and the like. In some embodiments, binders are used to impart cohesive qualities to a tablet, ensuring that the tablet remains intact after compression. Suitable binder materials include, by way of non-limiting example, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), Veegum, and combinations thereof. In certain embodiments, diluents are utilized to increase the bulk of the tablet so that a practical size tablet is provided. Suitable diluents include, by way of non-limiting example, dicalcium phosphate, calcium sulfate, lactose, cellulose, kaolin, mannitol, sodium chloride, dry starch, powdered sugar and combinations thereof. In certain embodiments, lubricants are used to facilitate tablet manufacture; examples of suitable lubricants include, by way of non-limiting example, vegetable oils such as peanut oil, cottonseed oil, sesame oil, olive oil, corn oil, and oil of theobroma, glycerin, magnesium stearate, calcium stearate, stearic acid and combinations thereof. In some embodiments, disintegrants are used to facilitate disintegration of the tablet, and include, by way of non-limiting example, starches, clays, celluloses, algins, gums, crosslinked polymers and combinations thereof. Fillers include, by way of non-limiting example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. In certain embodiments, stabilizers are used to inhibit or retard drug decomposition reactions that include, by way of example, oxidative reactions. In certain embodiments, surfactants are anionic, cationic, amphoteric or nonionic surface active agents.

In some embodiments, enteroendocrine peptide secretion enhancing agents described herein are orally administered in association with a carrier suitable for delivery of the enteroendocrine peptide secretion enhancing agents to the distal gastrointestinal tract (e.g., distal ileum, colon, and/or rectum).

In certain embodiments, a composition described herein comprises an enteroendocrine peptide secretion enhancing agent in association with a matrix (e.g., a matrix comprising hypermellose) that allows for controlled release of an active agent in the distal part of the ileum and/or the colon. In some embodiments, a composition comprises a polymer that is pH sensitive (e.g., a MMX™ matrix from Cosmo Pharmaceuticals) and allows for controlled release of an active agent in the distal part of the ileum. Examples of such pH sensitive polymers suitable for controlled release include and are not limited to polyacrylic polymers (e.g., anionic polymers of methacrylic acid and/or methacrylic acid esters, e.g., Carbopol® polymers) that comprise acidic groups (e.g., —COOH, —SO$_3$H) and swell in basic pH of the intestine (e.g., pH of abut 7 to about 8). In some embodiments, a composition suitable for controlled release in the distal ileum comprises microparticulate active agent (e.g., micronized active agent). In some embodiments, a non-enzymatically degrading poly (dl-lactide-co-glycolide) (PLGA) core is suitable for delivery of an enteroendocrine peptide secretion enhancing agent (e.g., bile acid) to the distal ileum. In some embodiments, a dosage form comprising an enteroendocrine peptide secretion enhancing agent (e.g., bile acid) is coated with an enteric polymer (e.g., Eudragit® S-100, cellulose acetate phthalate, polyvinylacetate phthalate, hydroxypropylmethylcellulose phthalate, anionic polymers of methacrylic acid, methacrylic acid esters or the like) for site specific delivery to the distal ileum and/or the colon. In some embodiments, bacterially activated systems are suitable for targeted delivery to the distal part of the ileum. Examples of micro-flora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal microflora enzymes include bacterial glycosidases such as, for example, D-galactosidase, β-D-glucosidase, α-L-arabinofuranosidase, β-D-xylopyranosidase or the like.

The pharmaceutical composition described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences*, 20th Edition (2000), a film coating is provided around the formulation of the compound of Formula I. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

In certain embodiments, an oral formulation for use in any method described herein is, e.g., an enteroendocrine peptide secretion enhancing agent in association with a labile bile acid sequestrant. A labile bile acid sequestrant is a bile acid sequestrant with a labile affinity for bile acids. In certain embodiments, a bile acid sequestrant described herein is an agent that sequesters (e.g., absorbs or is charged with) bile acid, and/or the salts thereof.

In specific embodiments, the labile bile acid sequestrant is an agent that sequesters (e.g., absorbs or is charged with) bile acid, and/or the salts thereof, and releases at least a portion of the absorbed or charged bile acid, and/or salts thereof in the distal gastrointestinal tract (e.g., the colon, ascending colon, sigmoid colon, distal colon, rectum, or any combination thereof). In certain embodiments, the labile bile acid sequestrant is an enzyme dependent bile acid sequestrant. In specific embodiments, the enzyme is a bacterial enzyme. In some embodiments, the enzyme is a bacterial enzyme found in high concentration in human colon or rectum relative to the concentration found in the small intestine. Examples of microflora activated systems include dosage forms comprising pectin, galactomannan, and/or Azo hydrogels and/or glycoside conjugates (e.g., conjugates of D-galactoside, β-D-xylopyranoside or the like) of the active agent. Examples of gastrointestinal micro-flora enzymes include bacterial glycosidases such as, for example, D-galactosidase, β-D-glucosidase, α-L-arabinofuranosidase, β-D-xylopyranosidase or the like. In some embodiments, the labile bile acid sequestrant is a time dependent bile acid sequestrant (i.e., the bile acid sequesters the bile acid and/or salts thereof and after a time releases at least a portion of the bile acid and/or salts thereof). In some embodiments, a time dependent bile acid sequestrant is an agent that degrades in an aqueous environment over time. In certain embodiments, a labile bile acid sequestrant described herein is a bile acid sequestrant that has a low affinity for bile acid and/or salts thereof, thereby allowing the bile acid sequestrant to continue to sequester bile acid and/or salts thereof in an environ where the bile acids and/or salts thereof are present in high concentration and release them in an environ wherein bile acids and/or salts thereof are present in a lower relative concentration. In some embodiments, the labile bile acid sequestrant has a high affinity for a primary bile acid and a low affinity for a secondary bile acid, allowing the bile acid sequestrant to sequester a primary bile acid or salt thereof and subsequently release a secondary bile acid or salt thereof as the primary bile acid or salt thereof is converted (e.g., metabolized) to the secondary bile acid or salt thereof. In some embodiments, the labile bile acid sequestrant is a pH dependent bile acid sequestrant. In some embodiments, the pH dependent bile acid sequestrant has a high affinity for bile acid at a pH of 6 or below and a low affinity for bile acid at a pH above 6. In certain embodiments, the pH dependent bile acid sequestrant degrades at a pH above 6.

In some embodiments, labile bile acid sequestrants described herein include any compound, e.g., a macro-structured compound, that can sequester bile acids and/or salts thereof through any suitable mechanism. For example, in certain embodiments, bile acid sequestrants sequester bile acids and/or salts thereof through ionic interactions, polar interactions, static interactions, hydrophobic interactions, lipophilic interactions, hydrophilic interactions, steric interactions, or the like. In certain embodiments, macrostructured compounds sequester bile acids and/or sequestrants by trapping the bile acids and/or salts thereof in pockets of the macrostructured compounds and, optionally, other interactions, such as those described above. In some embodiments, bile acid sequestrants (e.g., labile bile acid sequestrants) include, by way of non-limiting example, lignin, modified lignin, polymers, polycationic polymers and copolymers, polymers and/or copolymers comprising any one or more of N-alkenyl-N-alkylamine residues; one or more N,N,N-trialkyl-N—(N'-alkenylamino)alkyl-azanium residues; one or more N,N,N-trialkyl-N-alkenyl-azanium residues; one or more alkenyl-amine residues; or a combination thereof, or any combination thereof.

Covalent Linkage of the Drug with a Carrier

In some embodiments, strategies used for colon targeted delivery include, by way of non-limiting example, covalent linkage of the enteroendocrine peptide secretion enhancing agents to a carrier, coating the dosage form with a pH-sensitive polymer for delivery upon reaching the pH environment of the colon, using redox sensitive polymers, using a time released formulation, utilizing coatings that are specifically degraded by colonic bacteria, using bioadhesive system and using osmotically controlled drug delivery systems.

In certain embodiments of such oral administration of a composition containing an enteroendocrine peptide secretion enhancing agents described herein involves covalent linking an enteroendocrine peptide secretion enhancing agent and carrier wherein upon oral administration the linked moiety remains intact in the stomach and small intestine. Upon entering the colon the covalent linkage is broken by the change in pH, enzymes, and/or degradation by intestinal microflora. In certain embodiments, the covalent linkage between the enteroendocrine peptide secretion enhancing agent and the carrier includes, by way of non-limiting example, azo linkage, glycoside conjugates, glucuronide conjugates, cyclodextrin conjugates, dextran conjugates, and amino-acid conjugates (high hydrophilicity and long chain length of the carrier amino acid).

Coating with Polymers: pH-Sensitive Polymers

In some embodiments, the oral dosage forms described herein are coated with an enteric coating to facilitate the delivery of an enteroendocrine peptide secretion enhancing agent to the colon and/or rectum. In certain embodiments, an enteric coating is one that remains intact in the low pH environment of the stomach, but readily dissolved when the optimum dissolution pH of the particular coating is reached which depends upon the chemical composition of the enteric coating. The thickness of the coating will depend upon the solubility characteristics of the coating material. In certain embodiments, the coating thicknesses used in such formulations described herein range from about 25 µm to about 200 µm.

In certain embodiments, the compositions or formulations described herein are coated such that an enteroendocrine peptide secretion enhancing agent of the composition or formulation is delivered to the colon and/or rectum without absorbing at the upper part of the intestine. In a specific embodiment, specific delivery to the colon and/or rectum is achieved by coating of the dosage form with polymers that degrade only in the pH environment of the colon. In alternative embodiments, the composition is coated with an enteric coat that dissolves in the pH of the intestines and an outer layer matrix that slowly erodes in the intestine. In some of such embodiments, the matrix slowly erodes until only a core composition comprising an enteroendocrine peptide secretion enhancing agent (and, in some embodiments, an absorption inhibitor of the agent) is left and the core is delivered to the colon and/or rectum.

In certain embodiments, pH-dependent systems exploit the progressively increasing pH along the human gastrointestinal tract (GIT) from the stomach (pH 1-2 which increases to 4 during digestion), small intestine (pH 6-7) at the site of digestion and it to 7-8 in the distal ileum. In certain embodiments, dosage forms for oral administration of the compositions described herein are coated with pH-sensitive polymer(s) to provide delayed release and protect the enteroendocrine peptide secretion enhancing agents from gastric fluid. In certain embodiments, such polymers are be able to withstand the lower pH values of the stomach and of the proximal part of the small intestine, but disintegrate at the neutral or slightly alkaline pH of the terminal ileum and/or ileocecal junction. Thus, in certain embodiments, provided herein is an oral dosage form comprising a coating, the coating comprising a pH-sensitive polymer. In some embodiments, the polymers used for colon and/or rectum targeting include, by way of non-limiting example, methacrylic acid copolymers, methacrylic acid and methyl methacrylate copolymers, Eudragit L100, Eudragit S100, Eudragit L-30D, Eudragit FS-30D, Eudragit L100-55, polyvinylacetate phthalate, hyrdoxypropyl ethyl cellulose phthalate, hyrdoxypropyl methyl cellulose phthalate 50, hyrdoxypropyl methyl cellulose phthalate 55, cellulose acetate trimelliate, cellulose acetate phthalate and combinations thereof.

In certain embodiments, oral dosage forms suitable for delivery to the colon and/or rectum comprise a coating that has a biodegradable and/or bacteria degradable polymer or polymers that are degraded by the microflora (bacteria) in the colon. In such biodegradable systems suitable polymers include, by way of non-limiting example, azo polymers, linear-type-segmented polyurethanes containing azo groups, polygalactomannans, pectin, glutaraldehyde crosslinked dextran, polysaccharides, amylose, guar gum, pectin, chitosan, inulin, cyclodextrins, chondroitin sulphate, dextrans, locust bean gum, chondroitin sulphate, chitosan, poly(-caprolactone), polylactic acid and poly(lactic-co-glycolic acid).

In certain embodiments of such oral administration of compositions containing one or more enteroendocrine peptide secretion enhancing agents described herein, the compositions are delivered to the colon without absorbing at the upper part of the intestine by coating of the dosage forms with redox sensitive polymers that are degraded by the microflora (bacteria) in the colon. In such biodegradable systems such polymers include, by way of non-limiting example, redox-sensitive polymers containing an azo and/or a disulfide linkage in the backbone.

In some embodiments, compositions formulated for delivery to the colon and/or rectum are formulated for time-release. In some embodiments, time release formulations resist the acidic environment of the stomach, thereby delaying the release of the enteroendocrine peptide secretion enhancing agents until the dosage form enters the colon and/or rectum.

In certain embodiments the time released formulations described herein comprise a capsule (comprising an enteroendocrine peptide secretion enhancing agent and an optional absorption inhibitor) with hydrogel plug. In certain embodiments, the capsule and hydrogel plug are covered by a water-soluble cap and the whole unit is coated with an enteric polymer. When the capsule enters the small intestine the enteric coating dissolves and the hydrogels plug swells and dislodges from the capsule after a period of time and the composition is released from the capsule. The amount of hydrogel is used to adjust the period of time to the release the contents.

In some embodiments, provided herein is an oral dosage form comprising a multi-layered coat, wherein the coat comprises different layers of polymers having different pH-sensitivities. As the coated dosage form moves along GIT the different layers dissolve depending on the pH encountered. Polymers used in such formulations include, by way of non-limiting example, polymethacrylates with appropriate pH dissolution characteristics, Eudragit® RL and Eudragit®RS (inner layer), and Eudragit® FS (outer layer). In other embodiments the dosage form is an enteric coated tablets having an outer shell of hydroxypropylcellulose or hydroxypropylmethylcellulose acetate succinate (HPMCAS).

In some embodiments, provided herein is an oral dosage form that comprises coat with cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and combinations thereof.

Combination Therapy

In certain embodiments, provided herein are combination therapies. In certain embodiments, the compositions described herein comprise an additional therapeutic agent. In some embodiments, the methods described herein comprise administration of a second dosage form comprising an additional therapeutic agent. In certain embodiments, combination therapies the compositions described herein are administered as part of a regimen. Therefore, additional therapeutic agents and/or additional pharmaceutical dosage form can be applied to a patient either directly or indirectly, and concomitantly or sequentially, with the compositions and formulations described herein.

In certain embodiments the compositions described herein are used in combination with at least one appetite suppressant (e.g., a 5HT transport inhibitor, a NE transport inhibitor, a CB-1 antagonist/inverse agonist, a ghrelin antagonist, a H3 antagonist/inverse agonist, a MCH1R antagonist, a MCH2R agonist/antagonist, a NPY1 antagonist, a NPY2 agonist, a mGluR5 antagonist, leptin, a leptin agonist/modulator, a leptin derivative, an opiod antagonist, an orexin antagonist, a BRS3 agonist, a CCK-A agonist, CNTF, a CNTF agonist/modulator, a CNTF derivative, a 5HT2c agonist, a Mc5r agonist, a monoamine reuptake inhibitor, a serotonin reuptake inhibitor, a GLP-1 agonist, axokine, fenfluramine, nalmafene, phentermine, rimonabant, sibutramine, topiramate, phytopharm compound 57, and combinations thereof). In certain embodiments the compositions or formulations described herein are used in combination with at least one metabolic rate enhancing agents (e.g., an ACC2 inhibitor, a β3 agonist, DGAT1 inhibitor, a DGAT2 inhibitor, a FAS inhibitor, a PDE inhibitor, a thyroid hormone β agonist, an UCP-1, 2, or 3 activator, an acyl-estrogen, a glucocorticoid antagonist, an 11β HSD-1 inhibitor, a Mc3r agonist, a SCD-1, oleoyl-estrone, 3-[(3,5,7-trimethyl-1-adamantyl)methyl]-6,7,8,9-tetr-ahydro-5H-[1,2,4]triazolo[4,3-a]azepine; 3-(1-adamantyl)-4-ethyl-5-(e-thylthio)-4H-1,2,4-triazole; 3-adamantanyl-4,5,6,7,8,9,10,11,12,3a-de-cahydro-1,2,4-triazolo[4,3-a][11]annulene, 3-(1-adamantyl)-5-(3,4,5-trimethoxyphenyl)-4-methyl-4H-1,2,4-triazole and combinations thereof). In some embodiments, an enteroendocrine peptide secretion enhancing agent is combined or administered with a phosphodiesterase inhibitor. In certain embodiments, an enteroendocrine peptide secretion enhancing agent is combined or administered with caffeine. In certain embodiments the compositions or formulations described herein are used in combination with at least one nutrient absorption inhibitors (e.g., a lipase inhibitor; a fatty acid transporter inhibitor; a dicarboxylate transporter inhibitor; a glucose transporter inhibitor; a phosphate transporter inhibitor; orlistat and combinations thereof). In certain embodiments the compositions or formulations described herein are used in combination with at least one appetite suppressant and at least one metabolic rate enhancing agents. In certain embodiments the compositions or formulations described herein are used in combination with at least one appetite suppressant and at least one nutrient absorption inhibitors. In certain embodiments the compositions or formulations described herein are used in combination with at least one nutrient absorption inhibitors and at least one metabolic rate enhancing agents. In certain embodiments the compositions or formulations described herein are used in combination with at least one appetite suppressant, at least one metabolic rate enhancing agents and at least one nutrient absorption inhibitors.

Figure 16:
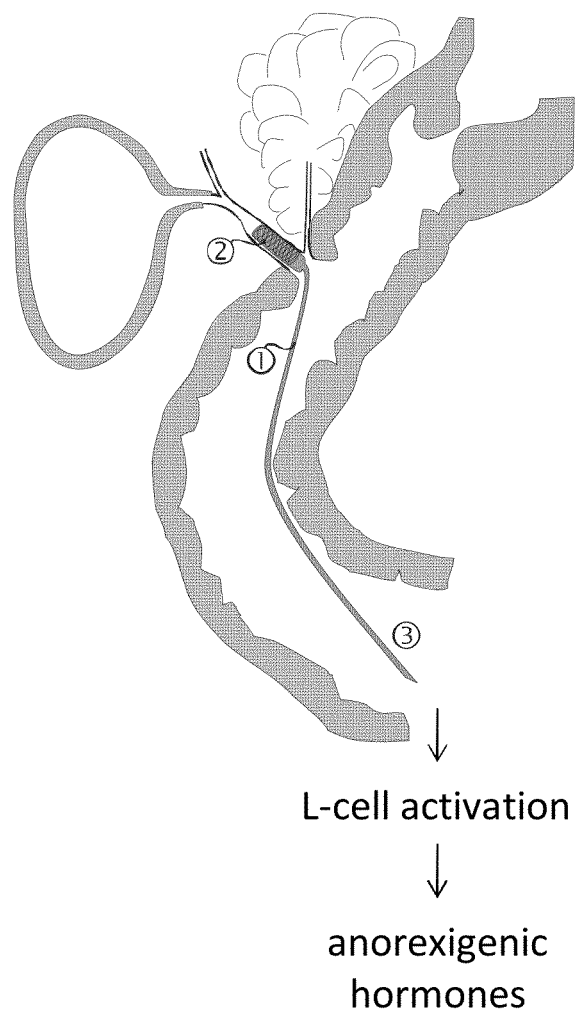
FIG. 16 illustrates delivery of bile acid salts to the lower gut via a biliary shunt.

In some embodiments, enteroendocrine peptide secretion enhancing agents therapies described herein are used in combination with biliary shunt treatments. In certain embodiments, a bilary shunt is a stented thin-walled catheter placed endoscopically within the common bile duct. In certain embodiments, the catheter runs a length down the gastrointestinal tract, providing for delivery of bile acids and/or salts to the distal gastrointestinal tract. FIG. 16 illustrates placement of a biliary shunt useful for delivery of endogenous bile acids and/or salts to the distal gastrointestinal tract (e.g., distal ileum, colon, and/or rectum).

In some embodiments, a combination described herein comprises a DPP-4 (used interchangeably herein with DPP-IV) inhibitor. In certain embodiments, a method described herein comprises administering a DPP-4 inhibitor. In some instances, inhibition of DPP-IV reduces the degradation of enteroendocrine peptide products (e.g. GLP-1) thereby prolonging the effect of GLP-1 in reducing blood glucose levels.

DPP-IV inhibitors suitable for use with the methods described herein include and are not limited to (2S)-1-{2-[(3-hydroxy-1-adamantyl)amino]acetyl}pyrrolidine-2-carbonitrile (vildagliptin), (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[3.1.0]hexane-3-carbonitrile (saxagliptin), and 2-({6-[(3R)-3-aminopiperidin-1-yl]-3-methyl-2,4-dioxo-3,4-dihydropyrimidin-1(2H)-yl}methyl)benzonitrile (alogliptin).

In some embodiments of any of the methods described herein, administration of an enteroendocrine peptide secretion enhancing agents described herein in combination with a DPP-IV inhibitor increases the level of GLP-1 in the blood and/or plasma of an individual by from about 1.1 times to about 30 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 1.1 times to about 20 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 1.5 times to about 10 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 2 times to about 8 times compared to the level of GLP-1 in the blood and/or plasma of the individual prior to administration of the enteroendocrine peptide secretion enhancing agent in combination with the DPP-IV inhibitor. In some embodiments of any of the methods described herein, administration of an enteroendocrine peptide secretion enhancing agent described herein in combination with a DPP-IV inhibitor increases the level of GLP-1 in the blood and/or plasma of an individual by from about 2 times to about 6 times compared to the level of GLP-1 in the blood and/or plasma of the individual prior to administration of the enteroendocrine peptide secretion enhancing agent in combination with the DPP-IV inhibitor. In some instances, an increase in GLP-1 level of from about 2 times to about 3 times following the administration of an enteroendocrine peptide secretion enhancing agent inhibitor described herein in combination with a DPP-IV inhibitor compared to the level of GLP-1 in the blood and/or plasma of the individual prior to administration of the enteroendocrine peptide secretion enhancing agent in combination with the DPP-IV inhibitor is associated with an anti-diabetic effect. In some instances, an increase in GLP-1 level of from about 3 times to about 8 times following the administration of an enteroendocrine peptide secretion enhancing agent described herein in combination with a DPP-IV inhibitor compared to the level of GLP-1 in the blood and/or plasma of the individual prior to administration of the enteroendocrine peptide secretion enhancing agent in combination with a DPP-IV inhibitor is associated with reduction in food intake and/or induction of satiety and/or weight loss.

In certain embodiments of any of the methods described herein, administration of an enteroendocrine peptide secretion enhancing agent in combination with a DPP-IV inhibitor reduces blood and/or plasma sugar levels by at least 20%, at least 30%, at least 40%, at least 50% at least 60%, at least 70% or at least 80% compared to blood and/or plasma sugar levels prior to administration of the enteroendocrine peptide secretion enhancing agent in combination with a DPP-IV inhibitor. In some embodiments of any of the methods described herein, administration of an enteroendocrine peptide secretion enhancing agent in combination with a DPP-IV inhibitor reduces blood and/or plasma sugar levels by at least 20% compared to blood and/or plasma sugar levels prior to administration of the enteroendocrine peptide secretion enhancing agent in combination with a DPP-IV inhibitor. In some embodiments of any of the methods described herein, administration of an enteroendocrine peptide secretion enhancing agent in combination with a DPP-IV inhibitor reduces blood and/or plasma sugar levels by at least 30% compared to blood and/or plasma sugar levels prior to administration of the enteroendocrine peptide secretion enhancing agent in combination with a DPP-IV inhibitor. In some embodiments of any of the methods described herein, administration of an enteroendocrine peptide secretion enhancing agent in combination with a DPP-IV inhibitor reduces blood and/or plasma sugar levels by at least 40% compared to blood and/or plasma sugar levels prior to administration of the enteroendocrine peptide secretion enhancing agent in combination with a DPP-IV inhibitor.

In some embodiments of any of the methods described herein, administration of an enteroendocrine peptide secretion enhancing agent in combination with a DPP-IV inhibitor reduces blood and/or plasma sugar levels for a longer period of time (e.g., at least 24 hours) compared to reduction in blood and/or plasma sugar levels upon administration of metformin in combination with a DPP-IV inhibitor. In some embodiments of any of the methods described herein, administration of a single dose of an enteroendocrine peptide secretion enhancing agent in combination with a DPP-IV inhibitor sustains reduced blood and/or plasma sugar levels for at least 6 hours, at least 12 hours, at least 14 hours, at least 16 hours, at least 18 hours, at least 20 hours, at least 24 hours, at least 30 hours, at least 36 hours or at least 48 hours compared to reduction in blood and/or plasma sugar levels upon administration of a single dose of metformin in combination with a DPP-IV inhibitor.

In some embodiments of any of the methods described herein, administration of an enteroendocrine peptide secretion enhancing agent in combination with a DPP-IV inhibitor results in higher levels of GLP-1 in blood and/or plasma of an individual compared to levels of GLP-1 in blood and/or plasma of a normal individual. In some embodiments of any of the methods described herein, administration of an enteroendocrine peptide secretion enhancing agent in combination with a DPP-IV inhibitor results in higher levels of GLP-1 in blood and/or plasma of an individual compared to levels of GLP-1 in blood and/or plasma of an individual undergoing therapy with metformin and/or a DPP-IV inhibitor.

Kits

In another aspect, provided herein are kits containing a device for rectal administration pre-filled a pharmaceutical composition described herein. In certain embodiments, kits contain a device for rectal administration and a pharmaceutical composition (e.g., a rectal dosage form) as described herein. In certain embodiments the kits includes prefilled bags for administration of rectal enemas, while in other embodiments the kits include prefilled bags for administration of rectal gels. In certain embodiments the kits includes prefilled syringes for administration of rectal enemas, while in other embodiments the kits include prefilled syringes for administration of rectal gels. In certain embodiments the kits includes prefilled pressurized cans for administration of rectal foams.

EXAMPLES

Example 1

Rectal Foams a) 500 mM Sodium Taurocholate
Preparation Method:
Using a stainless steel dissolving vessel fitted with a propeller stirrer and turboemulsifier 26.88 grams of sodium taurocholate, 0.25 grams of potassium metabisulphite, 0.3 grams EDTA (disodium salt), 0.38 grams of sodium benzoate and 0.2 grams of xanthan gum are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

b) 500 mM Sodium Glycocholate
Preparation Method:
Using a stainless steel dissolving vessel fitted with a propeller stirrer and turboemulsifier 24.38 grams of sodium glycocholate, 0.25 grams of potassium metabisulphite, 0.3 grams EDTA (disodium salt), 0.38 grams of sodium benzoate and 0.2 grams of xanthan gum are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

c) No Bile Salt (Control)
Preparation Method:
Using a stainless steel dissolving vessel fitted with a propeller stirrer and turboemulsifier 0.25 grams of potassium metabisulphite, 0.3 grams EDTA (disodium salt), 0.38 grams of sodium benzoate and 0.2 grams of xanthan gum are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

Analysis of Food Intake

The sodium taurocholate rectal foam described above is rectally administered to 5 conscious overnight-fasted subjects (e.g., Sprague Dawley rats) and the control rectal foam without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

The sodium glycocholate rectal foam described above is rectally administered to 5 conscious overnight-fasted subjects (e.g., Sprague Dawley rats) and the control rectal foam without the sodium taurocholate is rectally administered to 5 conscious overnight-fasted subject (e.g., Sprague Dawley rats). Each subject is exposed to pre-weighed food and the cumulative consumption of the food is determined over a 6 hour period by weighing the food every 30 minutes.

Example 2

Rectal Enemas a) 500 mM Sodium Taurocholate
Preparation Method:
Using a stainless steel dissolving vessel fitted with a propeller stirrer 26.88 grams of sodium taurocholate, 0.25 grams of potassium metabisulphite, 0.3 grams EDTA (disodium salt), 0.38 grams of sodium benzoate are dissolved in 100 mL of purified water and stirring is continued for 10 minutes. The solution is then pulled into a syringe.
b) 500 mM Sodium Glycocholate
Preparation Method:
Using a stainless steel dissolving vessel fitted with a propeller stirrer and turboemulsifier 24.38 grams of sodium glycocholate, 0.25 grams of potassium metabisulphite, 0.3 grams EDTA (disodium salt), 0.38 grams of sodium benzoate are dissolved in 100 mL of purified water and stirring is continued for 10 minutes. The solution is then pulled into a syringe.
c) No Bile Salt (Control)
Preparation Method:
Using a stainless steel dissolving vessel fitted with a propeller stirrer and turboemulsifier 0.25 grams of potassium metabisulphite, 0.3 grams EDTA (disodium salt), 0.38 grams of sodium benzoate are dissolved in 100 mL of purified water and stirring is continued for 10 minutes. The solution is then pulled into a syringe.
Analysis of Food Intake
The sodium taurocholate rectal enema described above is rectally administered to 5 conscious overnight-fasted subjects (e.g., Sprague Dawley rats) and the control rectal enema without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

The sodium glycocholate rectal enema described above is rectally administered to 5 conscious overnight-fasted subjects (e.g., Sprague Dawley rats) and the control rectal enema without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

Example 3

Rectal Suppositories a) Sodium Taurocholate
Preparation Method:
Using a stainless steel dissolving vessel fitted with a propeller stirrer 2.69 grams of sodium taurocholate and 0.1 grams of methyl cellulose are added to 10 grams of higher saturated fatty acid triglycerides (Witepsol™S55; Dynamic Novel Aktiengesellschaft, West Germany) and the combination is melted at 50 C and stirred. While the composition is a liquid it is filled into suppository containers for rats (50 mg per container) and then quenched in ice-water.
b) 500 mM Sodium Glycocholate
Preparation Method:
Using a stainless steel dissolving vessel fitted with a propeller stirrer 2.69 grams of sodium glycocholate and 0.1 grams of methyl cellulose are added to 10 grams of higher saturated fatty acid triglycerides (Witepsol™S55; Dynamic Novel Aktiengesellschaft, West Germany) and the combination is melted at 50 C and stirred. While the composition is a liquid it is filled into suppository containers for rats (50 mg per container) and then quenched in ice-water.
c) No Bile Salt (Control)
Preparation Method:
Using a stainless steel dissolving vessel fitted with a propeller stirrer 0.1 grams of methyl cellulose is added to 10 grams of higher saturated fatty acid triglycerides (Witepsol™S55; Dynamic Novel Aktiengesellschaft, West Germany) and the combination is melted at 50 C and stirred. While the composition is a liquid it is filled into suppository containers for rats (50 mg per container) and then quenched in ice-water.
Analysis of Food Intake
The sodium taurocholate rectal suppository described above is rectally administered to 5 conscious overnight-fasted subjects (e.g., Sprague Dawley rats) and the control rectal suppository without the sodium taurocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

The sodium glycocholate rectal suppository described above is rectally administered to 5 conscious overnight-fasted subjects (e.g., Sprague Dawley rats) and the control rectal suppository without the sodium glycocholate is rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes.

Example 4

Rectal Gels—Sodium Taurocholate/Control a) 500 mM Sodium Taurocholate
Preparation Method:
Using a stainless steel dissolving vessel fitted with a propeller stirrer 26.88 grams of sodium taurocholate and 1 gram of methyl cellulose are dissolved in 100 mL of purified water and stirred for 15 minutes. 6 syringes connected to gavage tubes were then each filled with 3 mL of the composition.
b) No Bile Salt (Control)
Preparation Method:
Using a stainless steel dissolving vessel fitted with a propeller stirrer 1 gram of methyl cellulose is dissolved in 100 mL of purified water and stirred for 15 minutes. 5 syringes connected to gavage tubes are then each filled with 3 mL of the composition.
Analysis of Food Intake
The sodium taurocholate rectal gel described above was rectally administered to 6 conscious overnight-fasted subjects (e.g., Sprague Dawley rats) and the control rectal gel without the sodium taurocholate was rectally administered to 5 conscious overnight-fasted subjects (e.g., Sprague Dawley rats). Each rat was then exposed to pre-weighed food and the cumulative consumption of the food was determined over a 6 hour period by weighing the food after 30 minutes, 60 minutes, 120 minutes, 240 minutes and 360 minutes.

Results

Figure 5:
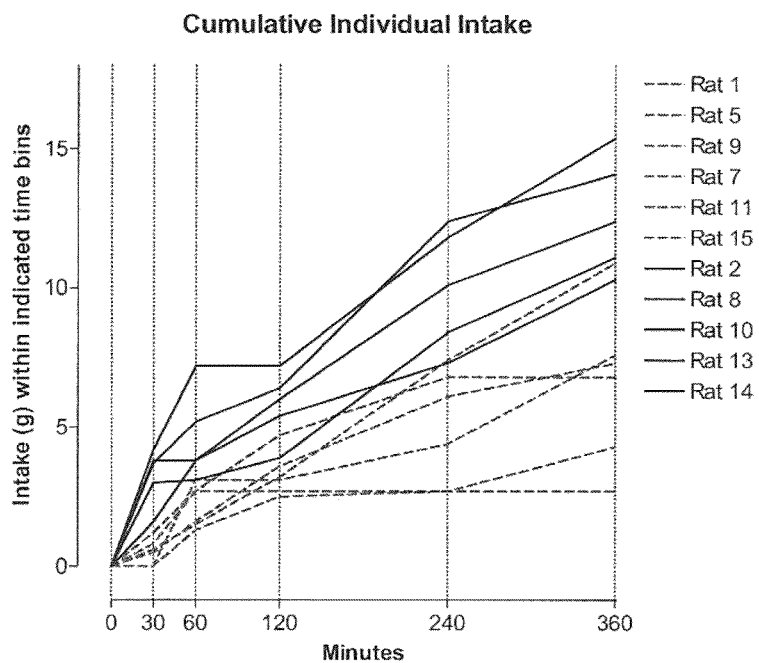
FIG. 5 illustrates the cumulative food intake of rats with (dotted lines) and without (solid lines) rectal administration of taurocholate.

The cumulative food intake in rats instilled with taurocholate containing gels is reduced compared to rats instilled with gel alone (FIG. 5). FIG. 5 illustrates the individual food intake in rats with bile sat containing gel per rectum (dotted lines) or control vehicle (solid lines). The effect of the taurocholate on food intake is found to be statistically significant.

Example 5

Rectal Gels—Sodium Taurcholate Dose Response a) 50 mM Sodium Taurocholate
Preparation Method:

Using a stainless steel dissolving vessel fitted with a propeller stirrer 2.688 grams of sodium taurocholate and 1 gram of methyl cellulose are dissolved in 100 mL of purified water and stirred for 15 minutes. 12 syringes connected to gavage tubes are then each filled with 3 mL of the composition.

b) 150 mM Sodium Taurocholate
Preparation Method:

Using a stainless steel dissolving vessel fitted with a propeller stirrer 8.066 grams of sodium taurocholate and 1 gram of methyl cellulose are dissolved in 100 mL of purified water and stirred for 15 minutes. 12 syringes connected to gavage tubes are then each filled with 3 mL of the composition.

c) 500 mM Sodium Taurocholate
Preparation Method:

Using a stainless steel dissolving vessel fitted with a propeller stirrer 26.88 grams of sodium taurocholate and 1 gram of methyl cellulose are dissolved in 100 mL of purified water and stirred for 15 minutes. 12 syringes connected to gavage tubes are then each filled with 3 mL of the composition.

d) No Bile Salt (Control)
Preparation Method:

Using a stainless steel dissolving vessel fitted with a propeller stirrer 1 gram of methyl cellulose is dissolved in 100 mL of purified water and stirred for 15 minutes. 12 syringes connected to gavage tubes are then each filled with 3 mL of the composition.

Analysis of Food Intake

A 4×4 Latin Square design is used to monitor the effect of the different concentration of taurocholate on the food uptake of overnight-fasted Sprague Dawley rats. Each concentration is tested in triplicate with four rats used per replicate. Therefore, twelve rats were used for each rectal gel composition (50 mM gel, 150 mM gel, 500 mM gel and the control gel), and all rats received each of the 4 treatments. Following rectal administration of the gels, each rat is then exposed to pre-weighed food and the cumulative consumption of the food is determined over a 24 hour period by weighing the food after 30 minutes, 1 hour, 2 hours, 4 hours, 6 hours, 8 hours and 24 hours.

Results

Figure 6:
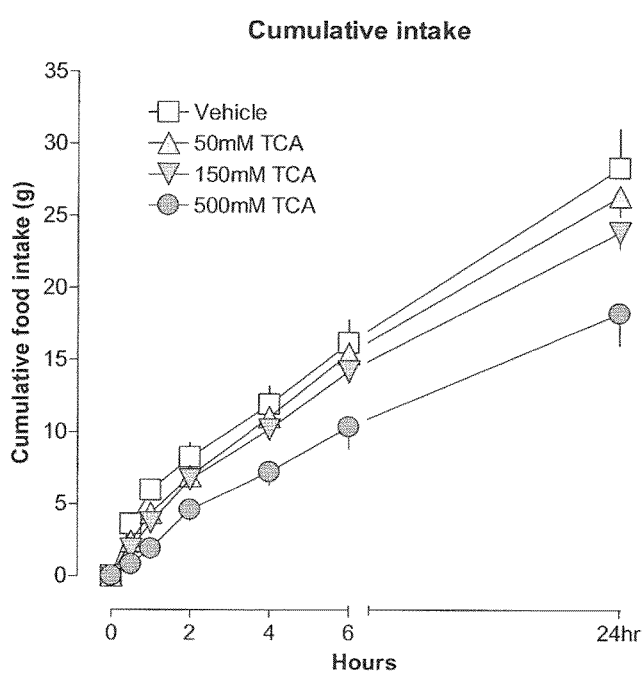
FIG. 6 illustrates the cumulative food intake of rats with rectal administration of three concentrations of taurocholate and the cumulative food intake of rats without rectal administration of taurocholate.

The cumulative food intake in rats instilled with taurocholate containing gels is observed to be dose dependently related to the quantity of taurocholate administered (FIG. 6). Moreover, the differences in food uptake are observed to be maintained for at least 24 hours.

Figure 7:
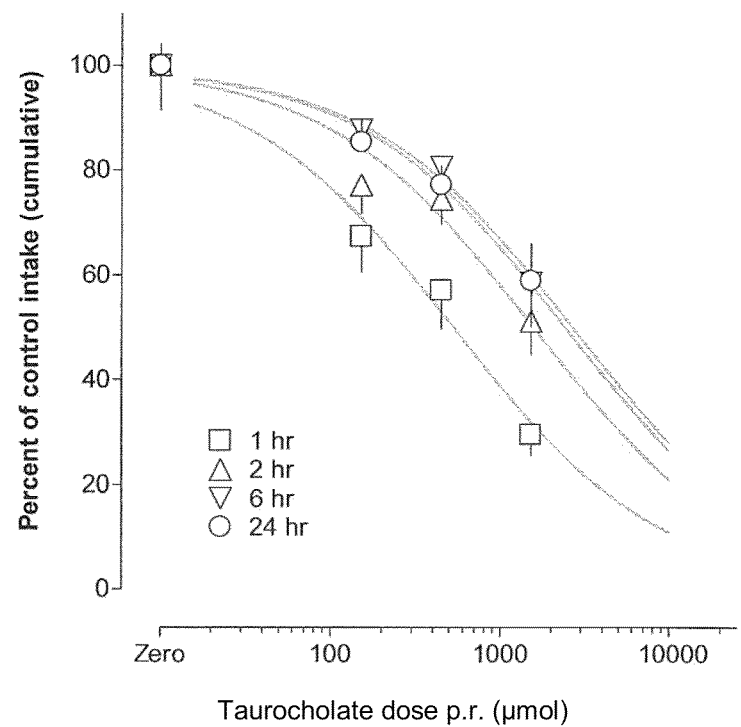
FIG. 7 illustrates the dose response for the anorectic effect of taurocholate.

The ED50 for inhibition of food intake is obtained by plotting th normalizing the dose response for the anorectic effect of taurocholate to the control data as a log of taurocholate dose vs the percentage of control cumulative intake (FIG. 7). The ED50 for inhibition of food intake at 1 hour is 528 mM for 3 mL doses (1.6 mmol/rat) while for 24 hour intake the ED50 is 7.2 mmol/rat. Surprisingly, the dose dependency for inhibition of intake is not different between 8 and 24 hours, thereby indicating the longevity of the anorectic response.

Example 6

Rectal Gels—Sodium Glycocholate/Control a) 500 mM Sodium Glycocholate
Preparation Method:

Using a stainless steel dissolving vessel fitted with a propeller stirrer 24.38 grams of sodium glucocholate and 1 gram of methyl cellulose are dissolved in 100 mL of purified water and then stirred for 15 minutes. 6 syringes connected to gavage tubes are then each filled with 3 mL of the composition.

b) No Bile Salt (Control)
Preparation Method:

Using a stainless steel dissolving vessel fitted with a propeller stirrer 1 gram of methyl cellulose is dissolved in 100 mL of purified water and stirred for 15 minutes. 5 syringes connected to gavage tubes are then each filled with 3 mL of the composition.

Analysis of Food Intake

The sodium glycocholate rectal gel described above is rectally administered to 6 conscious overnight-fasted subjects (e.g., Sprague Dawley rats) and the control rectal gel without the sodium glycocholate is rectally administered to 5 conscious overnight-fasted subjects (e.g., Sprague Dawley rats). Each subject is then exposed to pre-weighed food and the cumulative consumption of the food is determined over a 6 hour period by weighing the food after 30 minutes, 60 minutes, 120 minutes, 240 minutes and 360 minutes.

Example 7

Rectal Gels—Sodium Glycocholate Dose Response a) 50 mM Sodium Glycocholate
Preparation Method:

Using a stainless steel dissolving vessel fitted with a propeller stirrer 2.44 grams of sodium glycocholate and 1 gram of methyl cellulose are dissolved in 100 mL of purified water and then stirred for 15 minutes. 12 syringes connected to gavage tubes are then each filled with 3 mL of the composition.

b) 150 mM Sodium Glycocholate
Preparation Method:

Using a stainless steel dissolving vessel fitted with a propeller stirrer 7.32 grams of sodium glycocholate and 1 gram of methyl cellulose are dissolved in 100 mL of purified water and then stirred for 15 minutes. 12 syringes connected to gavage tubes are then each filled with 3 mL of the composition.

c) 500 mM Sodium Glycocholate
Preparation Method:

Using a stainless steel dissolving vessel fitted with a propeller stirrer 24.38 grams of sodium glycocholate and 1 gram of methyl cellulose are dissolved in 100 mL of purified water and then stirred for 15 minutes. 12 syringes connected to gavage tubes are then each filled with 3 mL of the composition.

d) No Bile Salt (Control)
Preparation Method:

Using a stainless steel dissolving vessel fitted with a propeller stirrer 1 gram of methyl cellulose is dissolved in 100 mL of purified water and then stirred for 15 minutes. 12 syringes connected to gavage tubes are then each filled with 3 mL of the composition.

Analysis of Food Intake

A 4×4 Latin Square design as used to monitor the effect of the different concentration of glycocholate on the food uptake of overnight-fasted Sprague Dawley rats. Each concentration is tested in triplicate with four rats used per replicate. Therefore, twelve rats are used for each rectal gel composition (50 mM gel, 150 mM gel, 500 mM gel and the control gel), with all rats receiving each of the 4 treatments. Following rectal administration of the gels, each rat is then exposed to pre-weighed food and the cumulative consumption of the food is determined over a 24 hour period by weighing the food after 30 minutes, 1 hour, 2 hours, 4 hours, 6 hours, 8 hours and 24 hours.

Example 8

Enteric Coated Tablets a) 5 mg Sodium Taurocholate
Preparation Method:

Preparation of core: 5 mg sodium taurocholate, 25 mg microcrystalline cellulose, 20 mg mannitol, and 10 mg croscarmellose sodium are mixed in a Hobart Mixer for 15 minutes. The mixture is granulated with 20% polyvinl pyrrolidone (4 mg) solution until optimum granulation is obtained. The granulation is dried overnight at 50° C. The granulation is then passed through a #30 mesh. The granulation is then blended with 1 mg magnesium stearate. Using an F-Press ¼" standard concave round punch, the granulation is compressed into a tablet. Preparation of erodible polymer layer and dual matrix tablets: 415 mg hydroxypropyl methylcellulose, 75 mg microcrystalline cellulose, and 6 mg polyvinylpyrrolidone are uniformly mixed with a mortar. The powder mix is granulated with 50% v/v alcohol solution until optimum granulation is obtained. The granulation is dried overnight at 50° C. The granulation is then passed through a #40 mesh screen. The granulation is then blended with 2.5 mg magnesium stearate. Using a Carver Press and a 7/16" standard concave round punch, half of the granulation is placed in the die cavity, the core is then placed in the cavity and the other half of the granulation is placed in the die cavity. The mass is compressed to 5,000 lbs to form the dual matrix tablet. Enteric coating: Using a propellar mixer, 42 g of hydroxypropyl methylcellulose phthalate and 4.2 g of distilled acetylated monoglycerides are dissolved in 514 mL of a mixture of a cetone and absolute alcohol (1:1). Using a spray system, the dual matrix tablets are then coated with the enteric coating solution. Approximately 60 mg of the coating material (dry basis) is applied per tablet.

b) 500 mM Sodium Glycocholate
Preparation Method:

Preparation of core: 5 mg sodium glycocholate, 25 mg microcrystalline cellulose, 20 mg mannitol, and 10 mg croscarmellose sodium are mixed in a Hobart Mixer for 15 minutes. The mixture is granulated with 20% polyvinl pyrrolidone (4 mg) solution until optimum granulation is obtained. The granulation is dried overnight at 50° C. The granulation is then passed through a #30 mesh. The granulation is then blended with 1 mg magnesium stearate. Using an F-Press ¼" standard concave round punch, the granulation is compressed into a tablet. Preparation of erodible polymer layer and dual matrix tablets: 415 mg hydroxypropyl methylcellulose, 75 mg microcrystalline cellulose, and 6 mg polyvinylpyrrolidone are uniformly mixed with a mortar. The powder mix is granulated with 50% v/v alcohol solution until optimum granulation is obtained. The granulation is dried overnight at 50° C. The granulation is then passed through a #40 mesh screen. The granulation is then blended with 2.5 mg magnesium stearate. Using a Carver Press and a 7/16" standard concave round punch, half of the granulation is placed in the die cavity, the core is then placed in the cavity and the other half of the granulation is placed in the die cavity. The mass is compressed to 5,000 lbs to form the dual matrix tablet. Enteric coating: Using a propellar mixer, 42 g of hydroxypropyl methylcellulose phthalate and 4.2 g of distilled acetylated monoglycerides are dissolved in 514 mL of a mixture of a cetone and absolute alcohol (1:1). Using a spray system, the dual matrix tablets are then coated with the enteric coating solution. Approximately 60 mg of the coating material (dry basis) is applied per tablet.

c) No Bile Salt (Control)
Preparation Method:

Preparation of core: 25 mg microcrystalline cellulose, 20 mg mannitol, and 10 mg croscarmellose sodium are mixed in a Hobart Mixer for 15 minutes. The mixture is granulated with 20% polyvinl pyrrolidone (4 mg) solution until optimum granulation is obtained. The granulation is dried overnight at 50° C. The granulation is then passed through a #30 mesh. The granulation is then blended with 1 mg magnesium stearate. Using an F-Press ¼" standard concave round punch, the granulation is compressed into a tablet. Preparation of erodible polymer layer and dual matrix tablets: 415 mg hydroxypropyl methylcellulose, 75 mg microcrystalline cellulose, and 6 mg polyvinylpyrrolidone are uniformly mixed with a mortar. The powder mix is granulated with 50% v/v alcohol solution until optimum granulation is obtained. The granulation is dried overnight at 50° C. The granulation is then passed through a #40 mesh screen. The granulation is then blended with 2.5 mg magnesium stearate. Using a Carver Press and a 7/16" standard concave round punch, half of the granulation is placed in the die cavity, the core is then placed in the cavity and the other half of the granulation is placed in the die cavity. The mass is compressed to 5,000 lbs to form the dual matrix tablet. Enteric coating: Using a propellar mixer, 42 g of hydroxypropyl methylcellulose phthalate and 4.2 g of distilled acetylated monoglycerides are dissolved in 514 mL of a mixture of a cetone and absolute alcohol (1:1). Using a spray system, the dual matrix tablets are then coated with the enteric coating solution. Approximately 60 mg of the coating material (dry basis) is applied per tablet.

Analysis of Food Intake

The sodium taurocholate tablet described above (or, when necessary given the size and identity of a subject, a similar tablet having an appropriate dose and size) is orally administered to 5 conscious overnight-fasted subjects and the control tablet without the sodium taurocholate is orally administered to 5 conscious overnight-fasted subjects. Each subject is exposed to pre-weighed food and the cumulative consumption of the food is determined over a 6 hour period by weighing the food every 30 minutes.

The sodium glycocholate tablet described above (or, when necessary given the size and identity of a subject, a similar tablet having an appropriate dose and size) is orally administered to 5 conscious overnight-fasted subjects and the control tablet without the sodium taurocholate is orally administered to 5 conscious overnight-fasted subjects. Each subject is exposed to pre-weighed food and the cumulative consumption of the food is determined over a 6 hour period by weighing the food every 30 minutes.

Example 9

Absorption Inhibitors a) Control: 500 mM Sodium Taurocholate
Preparation Method:

Using a stainless steel dissolving vessel fitted with a propeller stirrer and turboemulsifier 26.88 grams of sodium taurocholate, 0.25 grams of potassium metabisulphite, 0.3 grams EDTA (disodium salt) and 0.38 grams of sodium benzoate dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

b) 500 mM Sodium Taurocholate+Candidate Absorption Inhibitor
Preparation Method:

Using a stainless steel dissolving vessel fitted with a propeller stirrer and turboemulsifier 26.88 grams of sodium taurocholate, 0.25 grams of potassium metabisulphite, 0.3 grams EDTA (disodium salt), 0.38 grams of sodium benzoate and between 0.01 grams and 20 grams of a candidate absorption inhibitor are dissolved in 100 mL of purified water. While stirring, 4 grams of Polysorbate 20 and 4 grams of Polyglycol 300 isostearate are added and stirring is continued for 15 minutes. The suspension is then pumped into an aerosol cans and is immediately sealed by clinching the dispenser valve. The can is then pressurized by pumping 6.5 grams of Freon 12 and 3.5 grams of Freon 114 into the can.

Analysis of Absorption Inhibition

The foams described above are rectally administered to 5 conscious overnight-fasted subjects (e.g., Sprague Dawley rats). Each subject is exposed to pre-weighed food and the cumulative consumption of the food is determined over a 6 hour period by weighing the food every 30 minutes. Food intake is compared between the groups. The candidate absorption inhibitor inhibits absorption of the enteroendocrine peptide secretion enhancing agent (in this case sodium taurocholate) when the enteroendocrine peptide secretion enhancing agent is able to interact with the L-cells for a longer period of time (i.e., when it is not systemically absorbed), thereby reducing food intake when compared to the control formulation.

Alternatively, the ability of the absorption inhibitor to inhibit the absorption of the enteroendocrine peptide secretion enhancing agent (in this case sodium taurocholate) across the colon and/or rectum mucosa is determined by measuring the systemic concentration of enteroendocrine peptide secretion enhancing agent. Systemic concentration of enteroendocrine peptide secretion enhancing agent is measured prior to administration and at a time following administration of the enteroendocrine peptide secretion enhancing agent (e.g., after one hour). Decreased systemic concentration of the enteroendocrine peptide secretion enhancing agent indicate that the candidate absorption inhibitor inhibits the absorption of the enteroendocrine peptide secretion enhancing agent.

Example 10

Method of Inhibiting Food Intake

Studies are undertaken after an overnight fast following administration (8-10 hours prior to bile salt) of 100 mg Januvia (sitagliptin), a DDP-4 inhibitor that protects GLP-1 from inactivation by proteolysis. Dose escalation involves half-log increases in dose as tolerated. Planned doses are 1, 2, 7 and 20 mmoles of deoxycholic acid. Each dose is administered on a different day with at least three days between doses.

Subjects undergo complete physical examination with laboratory investigations including complete blood count, glucose, fasting lipids, liver function tests, urea and electrolytes, prothrombin time and partial thromboplastin time, haemoglobin $A_{1C}$, and urinalysis. Subjects are excluded if the fasting blood glucose is >300 mg/dl, if the haemoglobin $A_{1C}$ is >11%, or if there are abnormal liver function tests (such as transaminase levels >3× the upper limit of normal.

Subjects on oral medication will not receive such medication during the fasting period prior to the study or during the study period.

Subjects are studied on four separate occasions, e.g., at weekly intervals with at least three days gap between the different occasions. Subjects are studied after an overnight (10 hour) fast. Ten hours before the procedure, each subject will take 100 mg oral Januvia (sitagliptin), a DDP-4 inhibitor to protect GLP-1 (7-36) amide from degradation in the circulation. An indwelling catheter (Intracath) is placed in a forearm vein for blood sampling. An initial basal blood sample (5 ml) is taken and the catheter kept patent with normal saline. Blood samples are taken into EDTA Vacutainers (purple top). After 15 minutes a second blood sample (5 ml) will be collected. Placebo (vehicle) or sodium deoxycholate at doses of 1, 2, 7 and 20 mmoles, incorporated into 20 mL or 60 mL of 1% carboxymethyl cellulose is placed per rectum by syringe (type) over a period of one minute. Further 5 ml blood samples are collected 10, 20, 30, 40, 50 and 60 minutes after instillation of the placebo or deoxycholate.

In plasma samples from each time point we will measure glucose, insulin, GLP-1 (active) and PYY (total), using assay kits (Linco) from the Millipore Corporation. Measures of these hormones provide an endpoint for determining efficacy in producing reduced food intake.

In addition, measured is food intake for a two hour period after the end of the infusion study. During this period, the subjects are offered a buffet lunch with food in such excess that all appetites will be satisfied. The amount of food is quantified preprandially and postprandially and the caloric intake calculated. Before, at the end of the infusion study, and two hours after presentation of a buffet lunch, appetite ratings are made on a 100 mm visual analogue scale (higher values indicating greater appetite) with the text expressing the most positive and most negative ratings at each end of the scale.

Example 11

In certain instances, placing bile salts or other TGR5 agonists into the rectum has several advantages and provides substantial information on the whole process of releasing the distal gut hormones, GLP-1, oxyntomodulin and PYY. In our human studies we have demonstrated the following:

Dose-responsive increase in GLP-1 and PYY levels in the bloodstream.

Consequent increase in insulin secretion and reduction in glucose levels.

Dose-responsive and substantial reduction in food intake.

Elevation of high local concentrations of bile salt in the rectum without diarrhea.

Example 12

Studies were undertaken after an overnight fast following administration (8-10 hours prior to bile salt) of 100 mg sitagliptin, a DPP-4 inhibitor that protects GLP-1 from inactivation by proteolysis. Dose escalation involved half-log increases in dose of taurocholic acid. The doses used were 0.66, 2.0, 6.66 and 20.0 mmoles (358, 1075, 3584, 10,754 mg) of taurocholic acid. The taurocholic acid was administered into the rectum by syringe in a total volume of 20 ml of 1% carboxymethyl cellulose gel. Each dose was administered on a different day with at least three days between doses. FIG. 9 illustrates the increase of circulating GLP-1 levels following rectal administration of taurocholic acid. FIG. 10 illustrates the increase of circulating PYY levels following rectal administration of taurocholic acid.

What is claimed is:

1. A method for treating obesity or diabetes in an individual comprising non-systemically administering to the distal gastrointestinal tract of an individual in need thereof, a pharmaceutical composition consisting essentially of a therapeutically effective amount of an enteroendocrine peptide secretion enhancing agent, wherein the pharmaceutical composition is formulated for targeted delivery to the distal gastrointestinal tract and comprises at least one matrix and the enteroendocrine peptide secretion enhancing agent is a bile acid, bile salt, bile acid mimic or bile salt mimic.

2. The method of claim 1, wherein the pharmaceutical composition is administered rectally or orally.

3. The method of claim 1, wherein the enteroendocrine peptide secretion enhancing agent is a glucagon-like peptide secretion enhancing agent.

4. The method of claim 3, wherein the enteroendocrine peptide secretion enhancing agent is a glucagon-like peptide-1 (GLP-1) secretion enhancing agent or a glucagon-like peptide-2 (GLP-2) secretion enhancing agent.

5. The method of claim 1, wherein the enteroendocrine peptide secretion enhancing agent is a pancreatic polypeptide-fold peptide secretion enhancing agent.

6. The method of claim 5, wherein the enteroendocrine peptide secretion enhancing agent is a peptide YY (PYY) secretion enhancing agent.

7. The method of claim 1, wherein the pharmaceutical composition is non-systemically administered to at least the distal ileum.

8. The method of claim 1, wherein the pharmaceutical composition is non-systemically administered to at least the colon.

9. The method of claim 1, wherein the pharmaceutical composition is non-systemically administered to at least the rectum.

10. The method of claim 1, wherein the pharmaceutical composition is formulated as a tablet or capsule.

11. The method of claim 1, wherein the pharmaceutical composition is formulated as a dual matrix tablet.

* * * * *